United States Patent
Betelia et al.

(10) Patent No.: US 10,646,240 B2
(45) Date of Patent: May 12, 2020

(54) AORTIC LEAFLET REPAIR USING SHOCK WAVE APPLICATORS

(71) Applicant: SHOCKWAVE MEDICAL, INC., Fremont, CA (US)

(72) Inventors: Rainier Betelia, San Jose, CA (US); Hoa D. Nguyen, San Jose, CA (US); Camilo Perez Saaibi, Fremont, CA (US); Adam R. Tanner, Campbell, CA (US)

(73) Assignee: SHOCKWAVE MEDICAL, INC., Santa Clara, CA (US)

( * ) Notice: Subject to any disclaimer, the term of this patent is extended or adjusted under 35 U.S.C. 154(b) by 228 days.

(21) Appl. No.: 15/725,161

(22) Filed: Oct. 4, 2017

(65) Prior Publication Data

US 2018/0098779 A1    Apr. 12, 2018

Related U.S. Application Data

(60) Provisional application No. 62/405,002, filed on Oct. 6, 2016.

(51) Int. Cl.
*A61B 17/22* (2006.01)
*A61B 18/26* (2006.01)
(Continued)

(52) U.S. Cl.
CPC .. *A61B 17/22004* (2013.01); *A61B 17/22012* (2013.01); *A61B 17/22022* (2013.01);
(Continued)

(58) Field of Classification Search
CPC . A61B 17/22; A61B 17/221; A61B 17/22025; A61B 17/22031;
(Continued)

(56) References Cited

U.S. PATENT DOCUMENTS

| 3,413,976 A | 12/1968 | Voolfovich |
| 3,785,382 A | 1/1974 | Schmidt-Kloiber |

(Continued)

FOREIGN PATENT DOCUMENTS

| AU | 2009313507 B2 | 11/2014 |
| CN | 1269708 A | 10/2000 |

(Continued)

OTHER PUBLICATIONS

Advisory Action received for U.S. Appl. No. 14/229,735, dated Nov. 3, 2015, 3 pages.

(Continued)

*Primary Examiner* — Phong Son H Dang
(74) *Attorney, Agent, or Firm* — Morrison & Foerster LLP

(57) ABSTRACT

Described herein are shock wave devices and methods for the treatment of calcified heart valves. One variation of a shock wave device may comprise an elongated flexible tube carried by a sheath. The tube may have a fluid input end, which may be located near a proximal end of the sheath. The tube may include a loop portion. The loop portion may be configured to be at least partially accommodated within a cusp of the heart valve. The tube may be fillable with a conductive fluid. In some variations, the shock wave device may include an array of electrode pairs associated with a plurality of wires positioned within the loop portion of a tube. The electrode pairs may be electrically connectable to a voltage source and configured to generate shock waves in the conductive fluid in response to voltage pulses.

45 Claims, 19 Drawing Sheets

(51) Int. Cl.
*A61B 18/00* (2006.01)
*A61B 18/22* (2006.01)

(52) U.S. Cl.
CPC .... *A61B 18/26* (2013.01); *A61B 2017/22025* (2013.01); *A61B 2017/22079* (2013.01); *A61B 2017/22098* (2013.01); *A61B 2018/00369* (2013.01); *A61B 2018/2211* (2013.01); *A61B 2018/263* (2013.01); *A61B 2018/266* (2013.01)

(58) Field of Classification Search
CPC .......................................... A61B 2017/22089; A61B 2017/22091; A61B 2017/22098; A61B 17/22004; A61B 17/22022; A61B 17/22012; A61B 18/26; A61B 2017/22079; A61B 2018/266; A61B 2018/2211; A61B 2018/263; A61B 2018/00369
See application file for complete search history.

(56) References Cited

U.S. PATENT DOCUMENTS

| | | |
|---|---|---|
| 3,902,499 A | 9/1975 | Shene |
| 4,027,674 A | 6/1977 | Tessler et al. |
| 4,030,505 A | 6/1977 | Tessler |
| 4,662,126 A | 5/1987 | Malcolm |
| 4,671,254 A | 6/1987 | Fair |
| 4,685,458 A | 8/1987 | Leckrone |
| 4,809,682 A | 3/1989 | Forssmann et al. |
| 4,813,934 A | 3/1989 | Engelson et al. |
| 4,878,495 A | 11/1989 | Grayzel |
| 4,900,303 A | 2/1990 | Lemelson |
| 4,994,032 A | 2/1991 | Sugiyama et al. |
| 5,009,232 A | 4/1991 | Hassler et al. |
| 5,046,503 A | 9/1991 | Schneiderman |
| 5,057,103 A | 10/1991 | Davis |
| 5,057,106 A | 10/1991 | Kasevich et al. |
| 5,061,240 A | 10/1991 | Cherian |
| 5,078,717 A | 1/1992 | Parins et al. |
| 5,102,402 A | 4/1992 | Dror et al. |
| 5,103,804 A | 4/1992 | Abele et al. |
| 5,152,767 A | 10/1992 | Sypal et al. |
| 5,152,768 A | 10/1992 | Bhatta |
| 5,154,722 A | 10/1992 | Filip et al. |
| 5,176,675 A | 1/1993 | Watson et al. |
| 5,195,508 A | 3/1993 | Muller et al. |
| 5,245,988 A | 9/1993 | Einars et al. |
| 5,246,447 A | 9/1993 | Rosen et al. |
| 5,281,231 A | 1/1994 | Rosen et al. |
| 5,295,958 A | 3/1994 | Shturman |
| 5,324,255 A | 6/1994 | Passafaro et al. |
| 5,336,234 A | 8/1994 | Vigil et al. |
| 5,368,591 A | 11/1994 | Lennox et al. |
| 5,395,335 A | 3/1995 | Jang |
| 5,417,208 A | 5/1995 | Winkler |
| 5,425,735 A | 6/1995 | Rosen et al. |
| 5,472,406 A | 12/1995 | De La Torre et al. |
| 5,505,702 A | 4/1996 | Arney |
| 5,582,578 A | 12/1996 | Zhong et al. |
| 5,603,731 A | 2/1997 | Whitney |
| 5,609,606 A | 3/1997 | O'Boyle |
| 5,662,590 A | 9/1997 | De La Torre et al. |
| 5,846,218 A | 12/1998 | Brisken et al. |
| 5,893,840 A | 4/1999 | Hull et al. |
| 5,931,805 A | 8/1999 | Brisken |
| 6,007,530 A | 12/1999 | Dornhofer et al. |
| 6,033,371 A | 3/2000 | Torre et al. |
| 6,080,119 A | 6/2000 | Schwarze et al. |
| 6,083,232 A | 7/2000 | Cox |
| 6,113,560 A | 9/2000 | Simnacher |
| 6,146,358 A | 11/2000 | Rowe |
| 6,186,963 B1 | 2/2001 | Schwarze et al. |
| 6,210,408 B1 | 4/2001 | Chandrasekaran et al. |
| 6,217,531 B1 | 4/2001 | Reitmajer |
| 6,267,747 B1 | 7/2001 | Samson et al. |
| 6,277,138 B1 | 8/2001 | Levinson et al. |
| 6,287,272 B1 | 9/2001 | Brisken et al. |
| 6,352,535 B1 | 3/2002 | Lewis et al. |
| 6,367,203 B1 | 4/2002 | Graham et al. |
| 6,371,971 B1 | 4/2002 | Tsugita et al. |
| 6,398,792 B1 | 6/2002 | O'Connor |
| 6,406,486 B1 | 6/2002 | De La Torre et al. |
| 6,440,061 B1 | 8/2002 | Wenner et al. |
| 6,514,203 B2 | 2/2003 | Bukshpan |
| 6,524,251 B2 | 2/2003 | Rabiner et al. |
| 6,589,253 B1 | 7/2003 | Cornish et al. |
| 6,607,003 B1 | 8/2003 | Wilson |
| 6,638,246 B1 | 10/2003 | Naimark et al. |
| 6,652,547 B2 | 11/2003 | Rabiner et al. |
| 6,689,089 B1 | 2/2004 | Tiedtke et al. |
| 6,736,784 B1 | 5/2004 | Menne et al. |
| 6,740,081 B2 | 5/2004 | Hilal |
| 6,755,821 B1 | 6/2004 | Fry |
| 6,939,320 B2 | 9/2005 | Lennox |
| 6,989,009 B2 | 1/2006 | Lafontaine |
| 7,066,904 B2 | 6/2006 | Rosenthal et al. |
| 7,241,295 B2 | 7/2007 | Maguire |
| 7,505,812 B1 | 3/2009 | Eggers et al. |
| 7,569,032 B2 | 8/2009 | Naimark et al. |
| 7,618,432 B2 | 11/2009 | Pedersen et al. |
| 7,803,168 B2 | 9/2010 | Gifford et al. |
| 7,951,111 B2 | 5/2011 | Drasier et al. |
| 8,162,859 B2 | 4/2012 | Schultheiss et al. |
| 8,556,813 B2 | 10/2013 | Cioanta et al. |
| 8,574,247 B2 | 11/2013 | Adams et al. |
| 8,709,075 B2 | 4/2014 | Adams et al. |
| 8,728,091 B2 * | 5/2014 | Hakala ............. A61B 17/22022 606/128 |
| 8,747,416 B2 | 6/2014 | Hakala et al. |
| 8,888,788 B2 | 11/2014 | Hakala et al. |
| 8,956,371 B2 * | 2/2015 | Hawkins ............. A61B 17/2202 606/128 |
| 8,956,374 B2 | 2/2015 | Hawkins et al. |
| 9,005,216 B2 * | 4/2015 | Hakala ............. A61B 17/22022 606/128 |
| 9,011,462 B2 | 4/2015 | Adams et al. |
| 9,011,463 B2 * | 4/2015 | Adams ............. A61B 17/22022 606/128 |
| 9,044,618 B2 * | 6/2015 | Hawkins ........... A61M 25/1002 |
| 9,044,619 B2 | 6/2015 | Hawkins et al. |
| 9,180,280 B2 * | 11/2015 | Hawkins ............. A61B 17/2202 |
| 9,220,521 B2 | 12/2015 | Hawkins et al. |
| 9,289,224 B2 * | 3/2016 | Adams ............. A61B 17/22012 |
| 9,421,025 B2 | 8/2016 | Hawkins et al. |
| 9,522,012 B2 * | 12/2016 | Adams ............. A61B 17/22022 |
| 9,554,815 B2 | 1/2017 | Adams |
| 9,642,673 B2 * | 5/2017 | Adams ............. A61B 17/22022 |
| 2001/0044596 A1 | 11/2001 | Jaafar |
| 2002/0065512 A1 | 5/2002 | Fjield et al. |
| 2002/0177889 A1 | 11/2002 | Brisken et al. |
| 2003/0004434 A1 | 1/2003 | Greco et al. |
| 2003/0163081 A1 | 8/2003 | Constantz et al. |
| 2003/0176873 A1 | 9/2003 | Chernenko et al. |
| 2003/0229370 A1 | 12/2003 | Miller |
| 2004/0044308 A1 | 3/2004 | Naimark et al. |
| 2004/0082859 A1 | 4/2004 | Schaer |
| 2004/0097996 A1 | 5/2004 | Rabiner et al. |
| 2004/0181160 A1 * | 9/2004 | Rudy .................. A61B 5/0422 600/509 |
| 2004/0243107 A1 * | 12/2004 | Macoviak ............. A61B 90/50 606/1 |
| 2004/0249401 A1 | 12/2004 | Rabiner et al. |
| 2004/0254570 A1 | 12/2004 | Hadjicostis et al. |
| 2005/0015953 A1 | 1/2005 | Keidar |
| 2005/0021013 A1 | 1/2005 | Visuri et al. |
| 2005/0059965 A1 | 3/2005 | Eberl et al. |
| 2005/0075662 A1 | 4/2005 | Pedersen et al. |
| 2005/0090846 A1 | 4/2005 | Pedersen et al. |
| 2005/0090888 A1 | 4/2005 | Hines et al. |
| 2005/0113822 A1 | 5/2005 | Fuimaono et al. |
| 2005/0171527 A1 | 8/2005 | Bhola |
| 2005/0228372 A1 | 10/2005 | Truckai et al. |
| 2005/0245866 A1 | 11/2005 | Azizi |
| 2005/0251131 A1 | 11/2005 | Lesh |

(56) References Cited

U.S. PATENT DOCUMENTS

| | | |
|---|---|---|
| 2006/0004286 A1 | 1/2006 | Chang et al. |
| 2006/0069385 A1 | 3/2006 | Lafontaine et al. |
| 2006/0074484 A1 | 4/2006 | Huber |
| 2006/0178685 A1 | 8/2006 | Melsheimer |
| 2006/0184076 A1 | 8/2006 | Gill et al. |
| 2006/0190022 A1 | 8/2006 | Beyar et al. |
| 2007/0016112 A1 | 1/2007 | Schultheiss et al. |
| 2007/0088380 A1 | 4/2007 | Hirszowicz et al. |
| 2007/0118168 A1 | 5/2007 | Lointier et al. |
| 2007/0129667 A1 | 6/2007 | Tiedtke et al. |
| 2007/0239082 A1 | 10/2007 | Schultheiss et al. |
| 2007/0239253 A1 | 10/2007 | Jagger et al. |
| 2007/0244423 A1 | 10/2007 | Zumeris et al. |
| 2007/0299481 A1 | 12/2007 | Syed et al. |
| 2008/0033425 A1 | 2/2008 | Davis et al. |
| 2008/0077165 A1 | 3/2008 | Murphy |
| 2008/0097251 A1 | 4/2008 | Babaev |
| 2008/0188913 A1 | 8/2008 | Stone et al. |
| 2009/0030503 A1 | 1/2009 | Ho |
| 2009/0041833 A1 | 2/2009 | Bettinger et al. |
| 2009/0247945 A1 | 10/2009 | Levit et al. |
| 2009/0254114 A1 | 10/2009 | Hirszowicz et al. |
| 2009/0312768 A1 | 12/2009 | Hawkins et al. |
| 2010/0016862 A1 | 1/2010 | Hawkins et al. |
| 2010/0036294 A1 | 2/2010 | Mantell et al. |
| 2010/0094209 A1 | 4/2010 | Drasler et al. |
| 2010/0114020 A1 | 5/2010 | Hawkins et al. |
| 2010/0114065 A1 | 5/2010 | Hawkins et al. |
| 2010/0121322 A1 | 5/2010 | Swanson |
| 2010/0179424 A1 | 7/2010 | Warnking et al. |
| 2010/0305565 A1 | 12/2010 | Truckai et al. |
| 2010/0324554 A1 | 12/2010 | Gifford et al. |
| 2011/0034832 A1 | 2/2011 | Cioanta et al. |
| 2011/0118634 A1 | 5/2011 | Golan |
| 2011/0166570 A1 | 7/2011 | Hawkins et al. |
| 2011/0257523 A1 | 10/2011 | Hastings et al. |
| 2011/0295227 A1 | 12/2011 | Hawkins et al. |
| 2012/0071889 A1 | 3/2012 | Mantell et al. |
| 2012/0095461 A1 | 4/2012 | Herscher et al. |
| 2012/0116289 A1 | 5/2012 | Hawkins et al. |
| 2012/0143177 A1 | 6/2012 | Avitall |
| 2012/0143179 A1 | 6/2012 | Avitall |
| 2012/0203255 A1 | 8/2012 | Hawkins et al. |
| 2012/0221013 A1 | 8/2012 | Hawkins et al. |
| 2012/0253358 A1 | 10/2012 | Golan |
| 2013/0030431 A1 | 1/2013 | Adams |
| 2013/0030447 A1 | 1/2013 | Adams |
| 2013/0116714 A1 | 5/2013 | Adams et al. |
| 2013/0150874 A1 | 6/2013 | Kassab |
| 2014/0005576 A1 | 1/2014 | Adams et al. |
| 2014/0039513 A1 | 2/2014 | Hakala et al. |
| 2014/0039514 A1 | 2/2014 | Adams et al. |
| 2014/0046229 A1 | 2/2014 | Hawkins et al. |
| 2014/0046353 A1 | 2/2014 | Adams |
| 2014/0052145 A1 | 2/2014 | Adams et al. |
| 2014/0052147 A1 | 2/2014 | Hakala et al. |
| 2014/0074111 A1 | 3/2014 | Hakala et al. |
| 2014/0074113 A1 | 3/2014 | Hakala et al. |
| 2014/0163592 A1 | 6/2014 | Hakala et al. |
| 2014/0214061 A1 | 7/2014 | Adams et al. |
| 2014/0243820 A1 | 8/2014 | Adams et al. |
| 2014/0243847 A1 | 8/2014 | Hakala et al. |
| 2014/0288570 A1 | 9/2014 | Adams |
| 2014/0316428 A1* | 10/2014 | Golan ............... A61B 17/3207 606/128 |
| 2015/0073430 A1 | 3/2015 | Hakala et al. |
| 2015/0223757 A1* | 8/2015 | Werneth ............. A61B 5/6852 600/301 |
| 2015/0238208 A1 | 8/2015 | Adams et al. |
| 2015/0238209 A1 | 8/2015 | Hawkins et al. |
| 2015/0320432 A1 | 11/2015 | Adams |
| 2016/0135825 A1 | 5/2016 | Toler |
| 2016/0135828 A1 | 5/2016 | Hawkins et al. |
| 2016/0151081 A1 | 6/2016 | Adams et al. |
| 2016/0324534 A1 | 11/2016 | Hawkins et al. |
| 2017/0065227 A1* | 3/2017 | Marrs ................ A61B 5/0422 |
| 2017/0086867 A1 | 3/2017 | Adams |
| 2017/0303946 A1 | 10/2017 | Ku et al. |

FOREIGN PATENT DOCUMENTS

| | | |
|---|---|---|
| CN | 101043914 A | 9/2007 |
| CN | 102057422 A | 5/2011 |
| CN | 201906330 U | 7/2011 |
| CN | 102271748 A | 12/2011 |
| CN | 102765785 A | 11/2012 |
| DE | 3038445 A1 | 5/1982 |
| EP | 0442199 A2 | 8/1991 |
| EP | 0571306 A1 | 11/1993 |
| EP | 0623360 A1 | 11/1994 |
| EP | 2253884 A1 | 11/2010 |
| EP | 2362798 B1 | 4/2014 |
| JP | 60-191353 U | 12/1985 |
| JP | 62-99210 U | 6/1987 |
| JP | 62-275446 A | 11/1987 |
| JP | 3-63059 A | 3/1991 |
| JP | 6-125915 A | 5/1994 |
| JP | 7-47135 A | 2/1995 |
| JP | 8-89511 A | 4/1996 |
| JP | 10-99444 A | 4/1998 |
| JP | 10-314177 A | 12/1998 |
| JP | 10-513379 A | 12/1998 |
| JP | 2002-538932 A | 11/2002 |
| JP | 2004-81374 A | 3/2004 |
| JP | 2004-357792 A | 12/2004 |
| JP | 2005-95410 A | 4/2005 |
| JP | 2005-515825 A | 6/2005 |
| JP | 2005-518874 A | 6/2005 |
| JP | 2006-516465 A | 7/2006 |
| JP | 2007-532182 A | 11/2007 |
| JP | 2008-506447 A | 3/2008 |
| JP | 2011-513694 A | 4/2011 |
| JP | 2011-520248 A | 7/2011 |
| JP | 2011-524203 A | 9/2011 |
| JP | 2011-528963 A | 12/2011 |
| JP | 2012-505050 A | 3/2012 |
| JP | 2012-508042 A | 4/2012 |
| JP | 6029828 B2 | 11/2016 |
| JP | 6081510 B2 | 2/2017 |
| WO | 1989/11307 A1 | 11/1989 |
| WO | 1996/24297 A1 | 8/1996 |
| WO | 1999/02096 A1 | 1/1999 |
| WO | 2004/069072 A2 | 8/2004 |
| WO | 2005/099594 A1 | 10/2005 |
| WO | 2006/006169 A2 | 1/2006 |
| WO | 2006/127158 A2 | 11/2006 |
| WO | 2007/088546 A2 | 8/2007 |
| WO | 2007/149905 A2 | 12/2007 |
| WO | 2009/121017 A1 | 10/2009 |
| WO | 2009/126544 A1 | 10/2009 |
| WO | 2009/136268 A2 | 11/2009 |
| WO | 2009/152352 A2 | 12/2009 |
| WO | 2010/014515 A2 | 2/2010 |
| WO | 2010/054048 A2 | 5/2010 |
| WO | 2010/014515 A3 | 8/2010 |
| WO | 2010/054048 A3 | 9/2010 |
| WO | 2011/069025 A1 | 6/2011 |
| WO | 2011/143468 A2 | 11/2011 |
| WO | 2013/059735 A1 | 4/2013 |
| WO | 2013/070750 A1 | 5/2013 |
| WO | 2013085934 A1 | 6/2013 |
| WO | 2014/025620 A1 | 2/2014 |
| WO | 2016077627 A1 | 5/2016 |

OTHER PUBLICATIONS

Advisory Action received for U.S. Appl. No. 12/482,995, dated Jun. 2, 2014, 3 pages.

Advisory Action received for U.S. Appl. No. 12/482,995, dated Sep. 29, 2011, 2 pages.

Advisory Action received for U.S. Appl. No. 12/581,295, dated Jul. 3, 2014, 3 pages.

(56) References Cited

OTHER PUBLICATIONS

Advisory Action received for U.S. Appl. No. 13/049,199, dated Jun. 7, 2012, 3 pages.
Advisory Action received for U.S. Appl. No. 13/267,383, dated Jan. 6, 2014, 4 pages.
Cleveland et al., "The Physics of Shock Wave Lithotripsy", Extracorporeal Shock Wave Lithotripsy, Part IV, Chapter 38, 2012, pp. 317-332.
Connors et al., "Renal Nerves Mediate Changes in Contralateral Renal Blood Flow after Extracorporeal Shockwave Lithotripsy", Nephron Physiol, vol. 95, 2003, pp. 67-75.
Decision of Appeals Notice received for Japanese Patent Application No. 2011-534914, dated Oct. 17, 2016, 2 pages (Official Copy Only) (See Communication under 37 CFR § 1.98(a) (3)).
Decision to Grant received for European Patent Application No. 13756766.5, dated May 27, 2016, 2 pages.
Decision to Grant received for European Patent Application No. 09825393.3, dated Mar. 13, 2014, 2 pages.
Decision to Grant received for European Patent Application No. 13748228.7, dated Aug. 25, 2016, 2 pages.
Decision to Grant received for Japanese Patent Application No. 2011-513694, dated Oct. 7, 2014, 3 pages (Official Copy Only) (See Communication under 37 CFR § 1.98(a) (3)).
Extended European Search Report (includes Supplementary European Search Report and Search Opinion) received for European Patent Application No. 09763640.1, dated Oct. 10, 2013, 5 pages.
Extended European Search Report and Search Opinion received for European Patent Application No. 09825393.3, dated Feb. 28, 2013, 6 pages.
Extended European Search Report received for European Patent Application No. 13827971.6, dated Apr. 12, 2016, 8 pages.
Final Office Action received for U.S. Appl. No. 12/482,995, dated Jul. 22, 2011, 14 pages.
Final Office Action received for U.S. Appl. No. 12/501,619, dated Feb. 21, 2012, 12 pages.
Final Office Action received for U.S. Appl. No. 12/611,997, dated Dec. 11, 2012, 9 pages.
Final Office Action received for U.S. Appl. No. 12/611,997, dated Nov. 10, 2011, 15 pages.
Final Office Action received for U.S. Appl. No. 13/049,199, dated Apr. 4, 2012, 10 pages.
Final Office Action received for U.S. Appl. No. 13/207,381, dated Nov. 2, 2012, 7 pages.
Final Office Action received for U.S. Appl. No. 14/271,342 dated Feb. 27, 2015, 7 pages.
Final Office Action received for U.S. Appl. No. 12/482,995, dated Feb. 20, 2014, 11 pages.
Final Office Action received for U.S. Appl. No. 12/581,295, dated Jun. 5, 2014, 14 pages.
Final Office Action received for U.S. Appl. No. 12/611,997, dated Oct. 24, 2013, 10 pages.
Final Office Action received for U.S. Appl. No. 13/049,199, dated Aug. 11, 2014, 8 pages.
Final Office Action received for U.S. Appl. No. 13/207,381, dated Nov. 7, 2013, 7 pages.
Final Office Action received for U.S. Appl. No. 13/267,383, dated Oct. 25, 2013, 8 pages.
Final Office Action received for U.S. Appl. No. 13/534,658, dated Aug. 23, 2016, 11 pages.
Final Office Action received for U.S. Appl. No. 13/646,570, dated Dec. 23, 2014, 10 pages.
Final Office Action received for U.S. Appl. No. 13/962,315, dated Mar. 10, 2016, 25 pages.
Final Office Action received for U.S. Appl. No. 14/229,735, dated Aug. 27, 2015, 7 pages.
Final Office Action received for U.S. Appl. No. 14/660,539, dated Aug. 3, 2017, 11 pages.
Gambihler et al., "Permeabilization of the Plasma Membrane of L1210 Mouse Leukemia Cells Using Lithotripter Shock Waves", The Journal of Membrane Biology, vol. 141, 1994, pp. 267-275.
Grassi et al., "Novel Antihypertensive Therapies: Renal Sympathetic Nerve Ablation and Carotid Baroreceptor Stimulation", Curr Hypertens Rep, vol. 14, Sep. 26, 2012, pp. 567-572.
Intention to Grant received for European Patent Application No. 13748228.7, dated Mar. 23, 2016, 5 pages.
Intention to Grant received for European Patent Application No. 09763640.1, dated Oct. 11, 2017, 8 pages.
Intention to Grant received for European Patent Application No. 13756766.5, dated Jan. 8, 2016, 5 pages.
International Preliminary Report on Patentability received for PCT Patent Application No. PCT/US2011/051606, dated May 14, 2013, 6 pages.
International Preliminary Report on Patentability received for PCT Patent Application No. PCT/US2009/047070, dated Dec. 23, 2010, 7 pages.
International Preliminary Report on Patentability received for PCT Patent Application No. PCT/US2009/063354, dated May 19, 2011, 6 pages.
International Preliminary Report on Patentability received for PCT Patent Application No. PCT/US2011/047070, dated Feb. 21, 2013, 7 pages.
International Preliminary Report on Patentability received for PCT Patent Application No. PCT/US2012/023172, dated Aug. 15, 2013, 6 pages.
International Preliminary Report on Patentability received for PCT Patent Application No. PCT/US2012/063925, dated May 22, 2014, 12 pages.
International Preliminary Report on Patentability received for PCT Patent Application No. PCT/US2013/031805, dated Feb. 19, 2015, 11 pages.
International Preliminary Report on Patentability received for PCT Patent Application No. PCT/US2013/039987 dated Nov. 20, 2014, 11 pages.
International Preliminary Report on Patentability received for PCT Patent Application No. PCT/US2013/048277 dated Jan. 8, 2015, 9 pages.
International Preliminary Report on Patentability received for PCT Patent Application No. PCT/US2013/053292, dated Feb. 19, 2015, 9 pages.
International Preliminary Report on Patentability received for PCT Patent Application No. PCT/US2013/054104, dated Feb. 19, 2015, 8 pages.
International Preliminary Report on Patentability received for PCT Patent Application No. PCT/US2013/055431, dated Feb. 26, 2015, 7 pages.
International Preliminary Report on Patentability received for PCT Patent Application No. PCT/US2013/059533, dated Mar. 26, 2015, 10 pages.
International Preliminary Report on Patentability received for PCT Patent Application No. PCT/US2015/060453, dated May 26, 2017, 9 pages.
International Search Report and Written Opinion received for PCT Patent Application No. PCT/US2011/051606, dated Apr. 24, 2012, 9 pages.
International Search Report and Written Opinion received for PCT Patent Application No. PCT/US2013/031805 dated May 20, 2013, 13 pages.
International Search Report and Written Opinion received for PCT Patent Application No. PCT/US2013/039987, dated Sep. 23, 2013, 15 pages.
International Search Report and Written Opinion received for PCT Patent Application No. PCT/US2013/048277, dated Oct. 2, 2013, 14 pages.
International Search Report and Written Opinion received for PCT Patent Application No. PCT/US2013/053292, dated Nov. 4, 2013, 14 pages.
International Search Report and Written Opinion received for PCT Patent Application No. PCT/US2013/054104, dated Oct. 22, 2013, 12 pages.
International Search Report and Written Opinion received for PCT Patent Application No. PCT/US2013/055431, dated Nov. 12, 2013, 9 pages.

(56) References Cited

OTHER PUBLICATIONS

International Search Report and Written Opinion received for PCT Patent Application No. PCT/US2013/059533, dated Nov. 7, 2013, 14 pages.
International Search Report and Written Opinion received for PCT Patent Application No. PCT/US2015/060453, dated Jan. 21, 2016, 15 pages.
International Search Report and Written Opinion received for PCT Patent Application No. PCT/US2017/055070, dated Dec. 14, 2017, 16 pages.
International Search Report received for PCT Patent Application No. PCT/US2009/047070, dated Jan. 19, 2010, 4 pages.
International Search Report received for PCT Patent Application No. PCT/US2009/063354, dated Jun. 11, 2010, 3 pages.
International Search Report received for PCT Patent Application No. PCT/US2012/023172, dated Sep. 28, 2012, 3 pages.
International Search Report received for PCT Patent Application No. PCT/US2012/063925, dated Mar. 25, 2013, 3 pages.
International Written Opinion received for PCT Patent Application No. PCT/US2009/063354, dated Jun. 11, 2010, 4 pages.
International Written Opinion received for PCT Patent Application No. PCT/US2011/047070, dated May 1, 2012, 5 pages.
Kodama et al., "Shock wave-mediated molecular delivery into cells", Biochimica et Biophysica Acta, vol. 1542, 2002, pp. 186-194.
Lauer et al., "Shock Wave Permeabilization as a New Gene Transfer Method", Gene Therapy, vol. 4, 1997, pp. 710-715.
Non-Final Office Action received for U.S. Appl. No. 12/482,995, dated Aug. 13, 2014, 10 pages.
Non-Final Office Action received for U.S. Appl. No. 12/482,995, dated Jul. 12, 2013, 11 pages.
Non-Final Office Action received for U.S. Appl. No. 12/611,997, dated Nov. 26, 2014, 8 pages.
Non-Final Office Action received for U.S. Appl. No. 13/207,381, dated Nov. 25, 2014, 5 pages.
Non-Final Office Action received for U.S. Appl. No. 13/465,264, dated Oct. 29, 2014, 13 pages.
Non-Final Office Action received for U.S. Appl. No. 13/646,570, dated Oct. 29, 2014, 10 pages.
Non-Final Office Action received for U.S. Appl. No. 14/079,463, dated Mar. 4, 2014, 9 pages.
Non-Final Office Action received for U.S. Appl. No. 14/229,735, dated May 7, 2015, 8 pages.
Non-Final Office Action received for U.S. Appl. No. 12/482,995, dated Feb. 11, 2011, 27 pages.
Non-Final Office Action received for U.S. Appl. No. 12/501,619, dated Nov. 3, 2011, 10 pages.
Non-Final Office Action received for U.S. Appl. No. 12/611,997, dated Apr. 8, 2013, 9 pages.
Non-Final Office Action received for U.S. Appl. No. 12/611,997, dated Aug. 24, 2012, 11 pages.
Non-Final Office Action received for U.S. Appl. No. 12/611,997, dated Jun. 21, 2011, 13 pages.
Non-Final Office Action received for U.S. Appl. No. 13/049,199, dated Dec. 12, 2011, 10 pages.
Non-Final Office Action received for U.S. Appl. No. 13/207,381, dated Feb. 22, 2013, 7 pages.
Non-Final Office Action received for U.S. Appl. No. 13/207,381, dated Jun. 12, 2012, 6 pages.
Non-Final Office Action received for U.S. Appl. No. 13/232,730, dated Apr. 23, 2013, 10 pages.
Non-Final Office Action received for U.S. Appl. No. 13/291,875 dated Feb. 28, 2013, 8 pages.
Non-Final Office Action received for U.S. Appl. No. 13/534,658, dated Mar. 11, 2016, 12 pages.
Non-Final Office Action received for U.S. Appl. No. 14/515,130, dated Jan. 14, 2016, 16 pages.
Non-Final Office Action received for U.S. Appl. No. 12/501,619, dated Jan. 28, 2014, 10 pages.
Non-Final Office Action received for U.S. Appl. No. 12/581,295, dated Jan. 15, 2015, 14 pages.
Non-Final Office Action received for U.S. Appl. No. 12/581,295, dated Mar. 10, 2014, 11 pages.
Non-Final Office Action received for U.S. Appl. No. 12/611,997, dated Feb. 13, 2014, 9 pages.
Non-Final Office Action received for U.S. Appl. No. 13/049,199, dated Feb. 4, 2014, 8 pages.
Non-Final Office Action received for U.S. Appl. No. 13/207,381, dated Feb. 25, 2014, 8 pages.
Non-Final Office Action received for U.S. Appl. No. 13/267,383, dated Feb. 25, 2015, 9 pages.
Non-Final Office Action received for U.S. Appl. No. 13/465,264, dated Dec. 23, 2014, 13 pages.
Non-Final Office Action received for U.S. Appl. No. 13/646,583, dated Oct. 31, 2014, 8 pages.
Non-Final Office Action received for U.S. Appl. No. 13/962,315, dated Aug. 26, 2015, 20 pages.
Non-Final Office Action received for U.S. Appl. No. 14/061,554, dated Mar. 12, 2014, 14 pages.
Non-Final Office Action received for U.S. Appl. No. 14/271,276, dated Aug. 4, 2014, 7 pages.
Non-Final Office Action received for U.S. Appl. No. 14/271,342, dated Sep. 2, 2014, 6 pages.
Non-Final Office Action received for U.S. Appl. No. 14/660,539, dated Nov. 24, 2017, 10 pages.
Non-Final Office Action received for U.S. Appl. No. 14/693,155, dated Jan. 15, 2016, 6 pages.
Non-Final Office Action received for U.S. Appl. No. 15/213,105, dated Nov. 28, 2017, 7 pages.
Non-Final Office Action received for U.S. Appl. No. 14/660,539, dated Mar. 6, 2017, 14 pages.
Notice of Acceptance Received for Australian Patent Application No. 2009257368, dated Aug. 28, 2014, 2 pages.
Notice of Acceptance Received for Australian Patent Application No. 2009313507, dated Nov. 17, 2014, 2 pages.
Notice of Acceptance received for Australian Patent Application No. 2013299562, dated Jul. 3, 2017, 3 pages.
Notice of Allowance received for Canadian Patent Application No. 2,727,429, dated May 26, 2015, 1 page.
Notice of Allowance received for Canadian Patent Application No. 2,779,600, dated Jul. 7, 2017, 1 page.
Notice of Allowance received for Japanese Patent Application No. 2015-036444, dated Jan. 13, 2017, 3 pages (Official Copy Only) (See Communication under 37 CFR § 1.98(a) (3)).
Notice of Allowance received for Japanese Patent Application No. 2016-143049, dated Nov. 13, 2017, 3 pages (Official Copy Only) (See Communication under 37 CFR §1.98(a) (3)).
Notice of Allowance received for U.S. Appl. No. 14/229,735, dated Nov. 17, 2015, 5 pages.
Notice of Allowance received for U.S. Appl. No. 14/515,130, dated May 2, 2016, 8 pages.
Notice of Allowance received for U.S. Appl. No. 14/515,130, dated May 25, 2016, 3 pages.
Notice of Allowance received for U.S. Appl. No. 12/611,997, dated Apr. 15, 2015, 7 pages.
Notice of Allowance received for U.S. Appl. No. 13/207,381, dated Apr. 14, 2015, 7 pages.
Notice of Allowance received for U.S. Appl. No. 13/465,264, dated May 8, 2015, 7 pages.
Notice of Allowance received for U.S. Appl. No. 13/957,276, dated Aug. 28, 2015, 9 pages.
Notice of Allowance received for U.S. Appl. No. 14/046,635, dated Dec. 17, 2013, 7 pages.
Notice of Allowance received for U.S. Appl. No. 14/271,276, dated Feb. 25, 2015, 8 pages.
Notice of Allowance received for U.S. Appl. No. 12/482,995, dated Dec. 24, 2014, 6 pages.
Notice of Allowance received for U.S. Appl. No. 13/049,199, dated Dec. 15, 2014, 7 pages.
Notice of Allowance received for U.S. Appl. No. 13/049,199, dated Jan. 13, 2015, 4 pages.

(56) References Cited

OTHER PUBLICATIONS

Notice of Allowance received for U.S. Appl. No. 13/291,875, dated Sep. 17, 2013, 11 pages.
Notice of Allowance received for U.S. Appl. No. 13/646,570, dated Mar. 11, 2015, 7 pages.
Notice of Allowance received for U.S. Appl. No. 13/831,543, dated Oct. 8, 2014, 14 pages.
Notice of Allowance received for U.S. Appl. No. 13/962,315, dated Sep. 22, 2016, 12 pages.
Notice of Allowance received for U.S. Appl. No. 14/061,554, dated Apr. 25, 2014, 8 pages.
Notice of Allowance received for U.S. Appl. No. 14/079,463, dated Apr. 1, 2014, 5 pages.
Notice of Allowance received for U.S. Appl. No. 14/218,858, dated Aug. 26, 2016, 8 pages.
Notice of Allowance received for U.S. Appl. No. 14/271,342, dated Mar. 13, 2015, 5 pages.
Notice of Allowance received for U.S. Appl. No. 14/693,155, dated Apr. 26, 2016, 9 pages.
Office Action received for Japanese Patent Application No. 2016-143049, dated Jul. 28, 2017, 7 pages (4 pages of English Translation and 3 pages of Official Copy).
Office Action received for Australian Patent Application No. 2009257368, dated Apr. 28, 2014, 4 pages.
Office Action received for Australian Patent Application No. 2009257368, dated Jul. 31, 2013, 4 pages.
Office Action received for Australian Patent Application No. 2009313507, dated Nov. 13, 2013, 3 pages.
Office Action received for Australian Patent Application No. 2013299562, dated Jan. 20, 2017, 3 pages.
Office Action received for Canadian Patent Application No. 2,727,429, dated Apr. 14, 2015, 4 pages.
Office Action received for Canadian Patent Application No. 2,779,600, dated Jan. 4, 2016, 6 pages.
Office Action received for Canadian Patent Application No. 2,779,600, dated Oct. 19, 2016, 3 pages.
Office Action received for Chinese Patent Application No. 200980153687.X, dated Dec. 26, 2012, 11 pages (Official Copy Only) (See Communication under 37 CFR § 1.98(a) (3)).
Office Action received for Chinese Patent Application No. 200980153687.X, dated Jul. 11, 2013, 11 pages (Official Copy Only) (See Communication under 37 CFR § 1.98(a) (3)).
Office Action received for Chinese Patent Application No. 201380033808.3, dated Jul. 5, 2016, 9 pages (3 pages of English Translation and 6 pages of Official Copy).
Office Action received for Chinese Patent Application No. 201380041211.3, dated Aug. 14, 2017, 6 pages (2 pages of English Translation and 4 pages of Official Copy).
Office Action received for Chinese Patent Application No. 201380041211.3, dated Jul. 26, 2016, 12 pages (5 pages of English Translation and 7 pages of Official Copy).
Office Action received for Chinese Patent Application No. 201380041288.0, dated Jun. 20, 2016, 7 pages (4 pages of English Translation and 3 pages of Official Copy).
Office Action received for Chinese Patent Application No. 201380041656.1, dated Jul. 5, 2016, 9 pages (4 pages of English translation and 5 pages of Official Copy).
Office Action Received for Chinese Patent Application No. 201380041211.3, dated Mar. 20, 2017, 11 pages (5 pages of English translation and 6 pages of Official Copy).
Office Action received for Chinese Patent Application No. 201380042887.4, dated Aug. 8, 2016, 9 pages (4 pages of English translation and 5 pages of Official Copy).
Office Action received for European Patent Application No. 09763640.1, dated Dec. 2, 2016, 4 pages.
Office Action received for Japanese Patent Application No. 2011-513694, dated Aug. 27, 2013, 6 pages (3 pages of English Translation and 3 pages of Official Copy).
Office Action Received for Japanese Patent Application No. 2011-513694, dated Jun. 10, 2014, 4 pages total (2 pages of English Translation and 2 pages of Official Copy).
Office Action Received for Japanese Patent Application No. 2011-534914, dated Jan. 13, 2015, 9 pages (7 pages of English Translation and 2 pages of Official Copy).
Office Action Received for Japanese Patent Application No. 2011-534914, dated Jul. 15, 2014, 3 pages (1 page of English Translation and 2 pages of Official Copy).
Office Action received for Japanese Patent Application No. 2011-534914, dated May 10, 2016, 10 pages (6 pages of English Translation and 4 pages of Official Copy).
Office Action received for Japanese Patent Application No. 2011-534914, dated Oct. 1, 2013, 5 pages (2 pages of English Translation and 3 pages of Official Copy).
Office Action received for Japanese Patent Application No. 2014-158517, dated Feb. 15, 2017, 8 pages (5 pages of English Translation and 3 pages of Official Copy).
Office Action Received for Japanese Patent Application No. 2014-158517, dated Jun. 22, 2017, 14 pages (Official Copy Only) (See Communication under 37 CFR § 1.98(a) (3)).
Office Action received for Japanese Patent Application No. 2014-158517, dated May 19, 2015, 5 pages (2 pages of English Translation and 3 pages of Official Copy),
Office Action received for Japanese Patent Application No. 2015-036444, dated Feb. 23, 2016, 3 pages (English Translation Only).
Office Action received for Japanese Patent Application No. 2015-526700, dated Jun. 12, 2017, 14 pages (8 pages of English Translation and 6 pages of Official Copy).
Office Action received for Japanese Patent Application No. 2016-143049, dated Apr. 24, 2017, 5 pages (3 pages of English Translation and 2 pages of Official Copy).
Office Action received for Japanese Patent Application No. 2015-036444, dated Sep. 14, 2016, 5 pages (3 pages of English Translation and 2 pages of Official Copy).
Office Action received for Japanese Patent Application No. 2016-094326, dated Dec. 2, 2016, 4 pages (2 pages of English Translation and 2 pages Official Copy).
Office Action received for Japanese Patent Application No. 2016-094326, dated Jul. 6, 2017, 2 pages (Official Copy Only) (See Communication under 37 CFR § 1.98(a) (3)).
Rosenschein et al., "Shock-Wave Thrombus Ablation, a New Method for Noninvasive Mechanical Thrombolysis", The American Journal of Cardiology, vol. 70, Nov. 15, 1992, pp. 1358-1361.
Written Opinion received for PCT Patent Application No. PCT/US2012/023172, dated Sep. 28, 2012, 4 pages.
Written Opinion received for PCT Patent Application No. PCT/US2012/063925, dated Mar. 25, 2013, 9 pages.
Written Opinion received for PCT Patent Application No. PCT/US2009/047070, dated Jan. 19, 2010, 5 pages.
Zhong et al., "Transient Oscillation of Cavitation Bubbles Near Stone Surface During Electrohydraulic Lithotripsy", Journal of Endourology, vol. 11, No. 1, Feb. 1997, pp. 55-61.
Advisory Action received for U.S. Appl. No. 14/940,029, dated Jan. 24, 2019, 3 pages.
Final Office Action received for U.S. Appl. No. 14/940,029, dated Nov. 29, 2018, 17 pages.
Final Office Action received for U.S. Appl. No. 15/377,090, dated Mar. 05, 2019, 12 pages.
Intention to Grant received for European Patent Application No. 13750808.1, dated Mar. 7, 2018, 7 pages.
International Preliminary Report on Patentability received for PCT Patent Application No. PCT/US2017/055070, dated Apr. 18, 2019, 11 pages.
Non-Final Office Action received for U.S. Appl. No. 14/940,029, dated Apr. 04, 2019, 19 pages.
Non-Final Office Action received for U.S. Appl. No. 14/940,029, dated May 30, 2018, 28 pages.
Non-Final Office Action received for U.S. Appl. No. 15/377,090, dated Sep. 5, 2019, 12 pages.

(56) References Cited

OTHER PUBLICATIONS

Non-Final Office Action received for U.S. Appl. No. 15/377,090, dated Sep. 20, 2018, 12 pages.

* cited by examiner

AORTIC LEAFLET REPAIR USING SHOCK WAVE APPLICATORS

CROSS-REFERENCE TO RELATED APPLICATIONS

This application claims priority to U.S. Provisional Patent Application No. 62/405,002, filed Oct. 6, 2016, which is incorporated herein by reference in its entirety.

BACKGROUND

Aortic valve stenosis results in the narrowing of the aortic valve. Aortic valve stenosis may be exacerbated by a congenital defect where the aortic valve has one leaflet (unicuspid) or two leaflets (bicuspid) instead of three leaflets. In many cases, the narrowing of the aortic valve is the result of aortic valve calcification, where calcified plaque accumulates on the leaflets and/or annulus of the aortic valve. For example, calcium plaques deposited on the cusps of the leaflets may stiffen the leaflets, thereby narrowing the valve opening and interfering with efficient blood flow across the aortic valve.

Although research is underway in the development of a replacement aortic valve, one may prefer to soften the leaflets by modifying (e.g., reducing) or cracking the calcium deposits on the native valve instead of replacing it with an artificial valve. Accordingly, improved methods of softening a calcified aortic valve may be desirable.

BRIEF SUMMARY

Described herein are shock wave devices and methods for the treatment of calcified heart valves. The application of shock waves to a calcified region of a valve may help to crack and/or break the calcium deposits, thereby softening and/or loosening and/or removing calcium deposits that stiffen the mechanical properties of the valve. Softening and/or loosening and/or removing calcium deposits may allow the valve to regain at least a portion of its normal function. One embodiment of a shock wave device may comprise an elongated flexible tube carried by a sheath. The tube may have a fluid input end as well as fluid output end, which may be located near a proximal end of the sheath. The tube may include a loop portion located near a distal end of the sheath. The loop portion may be configured to be at least partially accommodated within a cusp of the heart valve. The tube may be fillable with a conductive fluid via the fluid input end of the tube. In some variations, the shock wave device may include an array of electrode pairs associated with a plurality of wires positioned within the loop portion of a tube. The electrode pairs may be electrically connectable to a voltage source and configured to generate shock waves in the conductive fluid in response to voltage pulses. Shock wave devices comprising at least two elongated flexible tubes and one or more electrode pairs may be used for treating unicuspid, bicuspid and/or tricuspid valves.

Methods for delivering shock waves to treat calcified lesions of a heart valve may comprise introducing a shock wave device into a patient's vasculature. The shock wave device may comprise an elongated flexible tube carried by a sheath. The tube may have a fluid input end. The fluid input end of the tube may be located near a proximal end of the sheath. The tube may include a loop portion located near a distal end of the sheath. The loop portion of the tube may be configured to be at least partially accommodated within a cusp of the heart valve. The tube may be fillable with a conductive fluid via the fluid input end of the tube. The shock wave device may comprise an array of electrode pairs associated with a plurality of wires positioned within the loop portion. The electrode pairs may be electrically connectable to a voltage source and configured to generate shock waves in the conductive fluid in response to voltage pulses. Methods for delivering shock waves to treat calcified lesions of a heart valve may further comprise advancing the shock wave device within the vasculature such that the loop portion of the tube is at least partially accommodated with a cusp of the heart valve; providing the tube of the shock wave device with conductive fluid; and activating the voltage source to apply a shock waves to treat the calcified lesions.

Other devices and methods that may be used to crack and/or break calcified deposits in an aortic valve (e.g., as part of a valvuloplasty procedure) are described in co-pending U.S. Pat. Pub. No. 2014/0046353 filed Aug. 8, 2013 (U.S. patent application Ser. No. 13/962,315); U.S. Pat. Pub. No. 2011/0295227 filed Aug. 10, 2011 (U.S. patent application Ser. No. 13/207,381, now U.S. Pat. No. 9,044,619), U.S. Pat. Pub. No. 2013/0116714 filed Nov. 8, 2011 (U.S. patent application Ser. No. 13/291,875, now U.S. Pat. No. 8,574,247), U.S. Pat. Pub. No. 2014/0163592 filed Aug. 1, 2013 (U.S. patent application Ser. No. 13/957,276, now U.S. Pat. No. 9,220,521 issued Dec. 29, 2015), which are hereby incorporated by reference in their entirety.

One variation for delivering shock waves to treat calcified lesions in a heart valve (e.g., a heart valve having a plurality of cusps each having a concave portion) may comprise an elongated flexible tube carried by a sheath. The tube may have a fluid input end, which may be located near a proximal end of the sheath. The tube may include a loop portion located near a distal end of the sheath. The loop portion may be configured to be at least partially accommodated within a cusp of the heart valve. The tube may be fillable with a conductive fluid via the fluid input end of the tube and subsequently purge used conductive fluid through the fluid output tube located on the sheath. The device may further comprise an elongated flexible support wire disposed within the tube and at least two insulated wires supported by the elongated flexible support wire. At least two insulated wires may be coiled around the flexible support wire. The device may further comprise at least two electrode pairs included in at least two insulated wires positioned within the loop portion. Each of the electrode pairs may comprise a plurality of spark-generating regions (or arc-generating regions) formed within interleaved portions of two insulated wires of the at least two insulated wires. The arc-generating regions are devoid of insulation. At least two electrode pairs may be electrically connectable to a voltage source and configured to generate shock waves in the conductive fluid in response to voltage pulses.

Any of the devices described herein may further comprise a plurality of spacers configured to space the array of electrode pairs away from the inner wall of the tube; a marker disposed in the loop portion of the tube; a fluid source, and a fluid pump. The fluid pump may be configured to deliver fluid from the fluid source to the fluid input end of the tube as well as remove fluid from the tube. To maintain the maximum shockwave output, it may be desirable to remove debris and air bubbles from the tube and replenish the tube with fresh conductive fluid. A pressure relief valve may be attached to the fluid output end so the pump can deliver the conductive fluid at a constant pressure. In some example, a pressure regulator may be attached at the fluid input end. Optionally, the device may further comprise at least one additional elongated flexible tube carried by the sheath, and a central anchor extending between and beyond the loop portions of the tubes and configured to pass through the leaflets of the heart valves and into the ventricle to stabilize the position of the sheath.

DETAILED DESCRIPTION

Figure 1A:
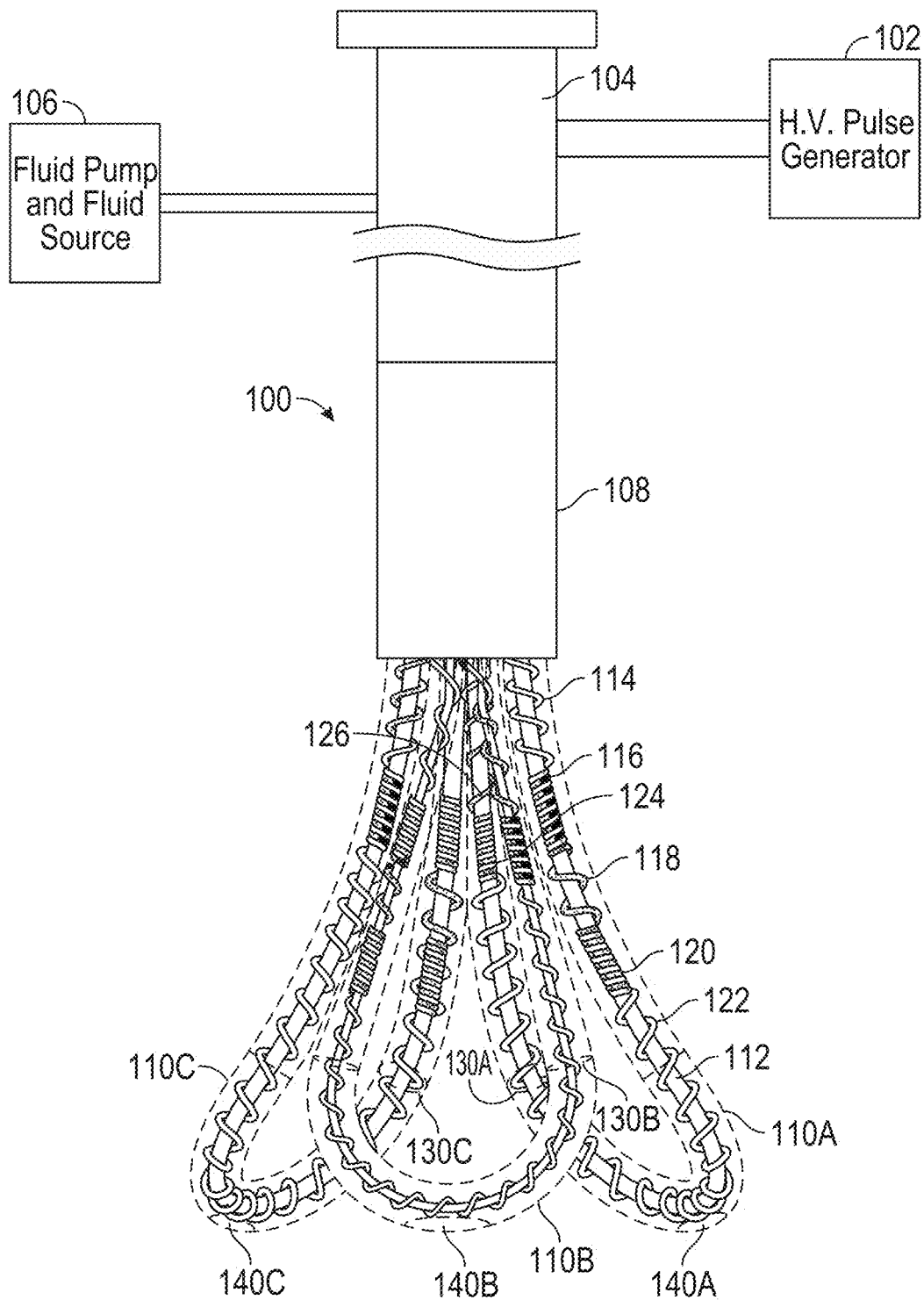
FIG. 1A schematically depicts one variation of a shock wave device for the treatment of calcified lesions in a heart valve.
Figure 1B:
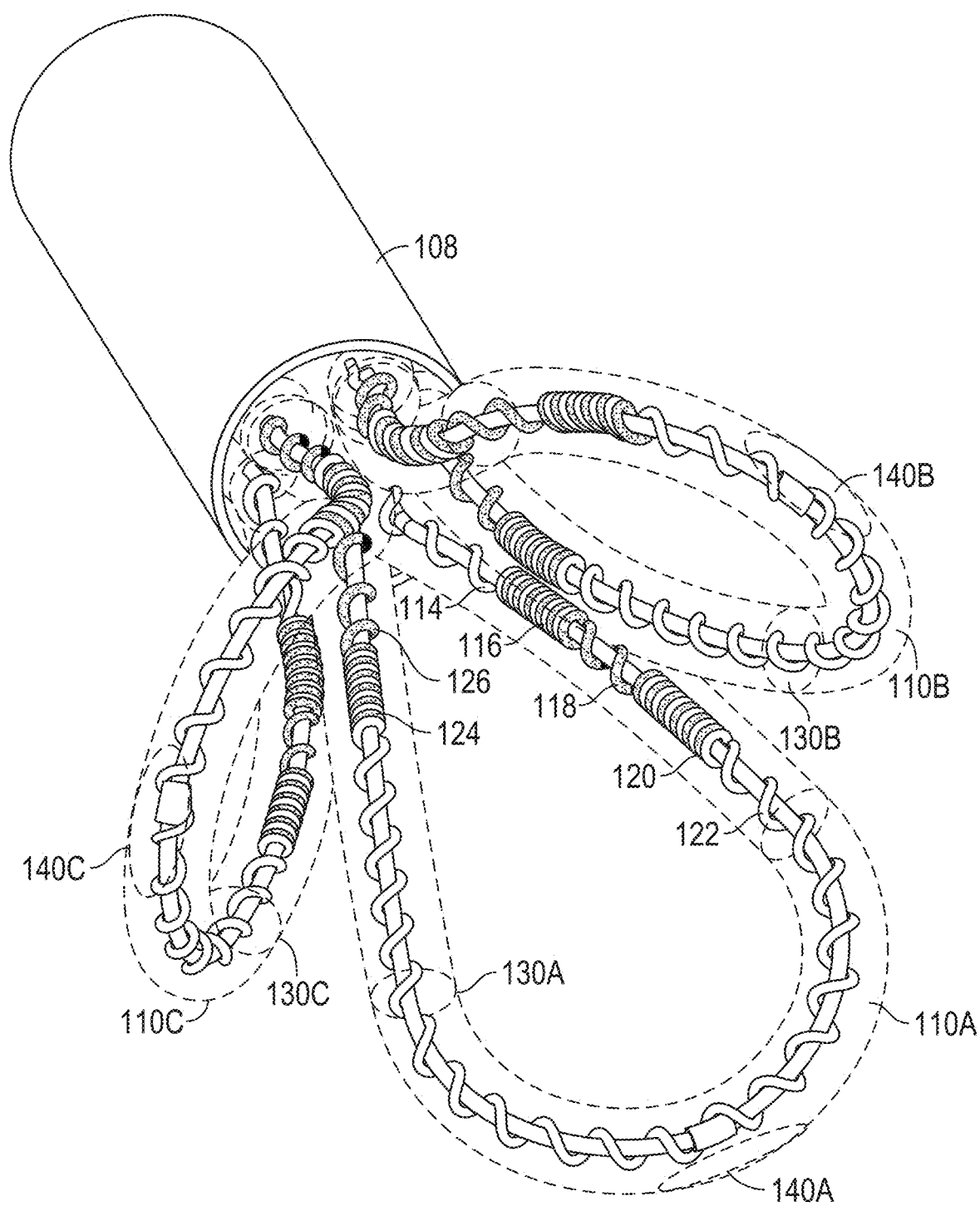
FIG. 1B schematically depicts exemplary elongated flexible tubes carried by a sheath.

FIG. 1A schematically depicts one variation of a shock wave device 100 for the treatment of calcified lesions in a heart valve. FIG. 1B schematically depicts exemplary elongated flexible tubes 110A-C carried by a sheath 108. The shock wave device 100 may comprise a first elongated flexible tube 110A, a second elongated flexible tube 110B, and a third elongated flexible tube 110C. As illustrated in FIGS. 1A-1B, the elongated flexible tubes 110A-C may be carried by a sheath 108. At least part of the elongated flexible tubes 110A-C may be movably accommodated within the sheath 108. As illustrated in FIGS. 1A-1B, one or more of the elongated flexible tubes 110A-C may be extended beyond the distal end of the sheath 108 for treating calcified lesions in heart valves. In some variations, the sheath 108 may be coupled to a proximal handle 104. The sheath 108 may be introduced into the vasculature and advanced in a retrograde direction (e.g., via a femoral artery) to a heart valve. The sheath 108 and the proximal handle 104 are similar to those described in more detail in co-pending U.S. patent application Ser. No. 13/962,315 filed Aug. 8, 2013 (U.S. Pat. Pub. No. 2014/0046353), which is hereby incorporated by reference in its entirety. While three elongated flexible tubes 110A-C are illustrated in FIGS. 1A-1B, it is appreciated that the shock wave device 100 may comprise any other numbers of elongated flexible tubes (e.g., one or two tubes).

Figure 1C:
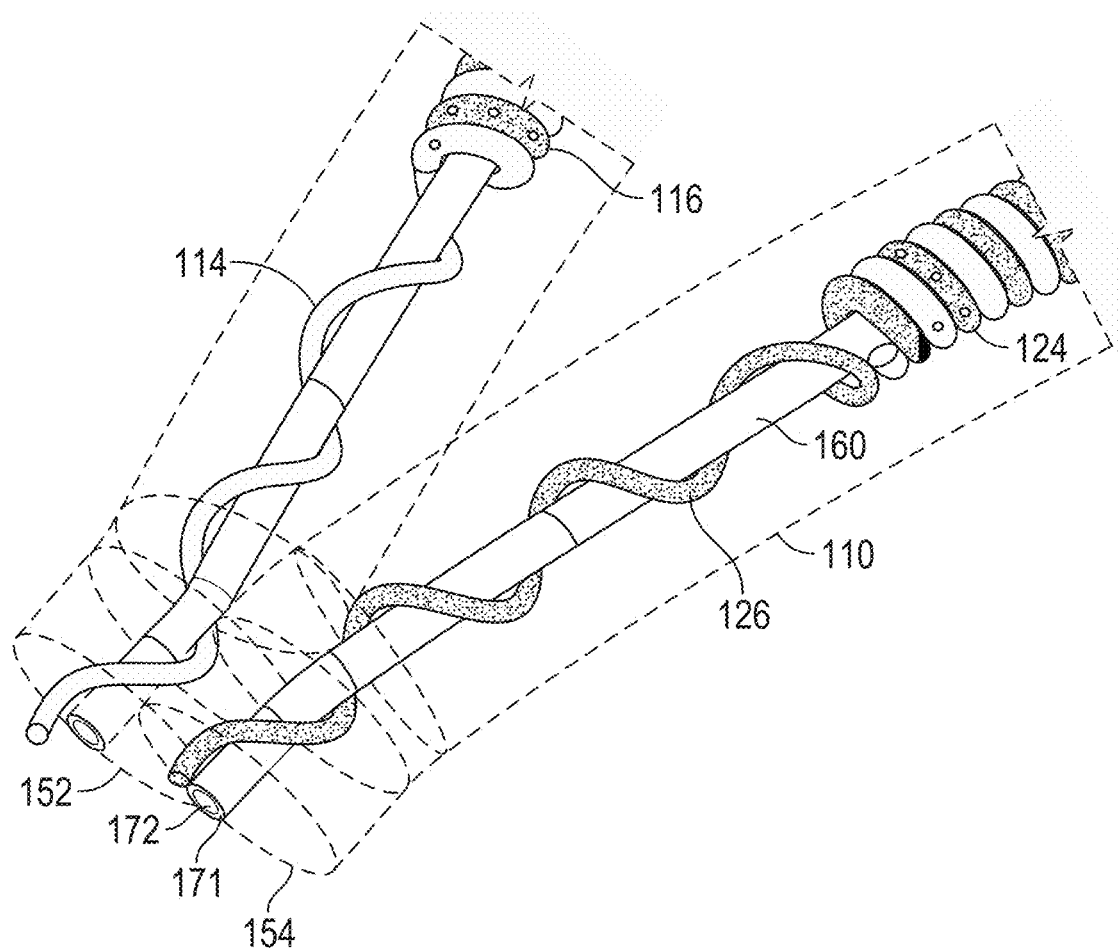
FIG. 1C depicts a partial, enlarged view of an exemplary elongated flexible tube of a shock wave device.

FIG. 1C depicts a partial, enlarged view of an exemplary flexible tube. As shown in FIG. 1C, in some variations, an elongated flexible tube 110 (e.g., 110A-C) may comprise a fluid input end 152 and a fluid output end 154. The fluid input end 152 and the fluid output end 154 may be located near a proximal end of the sheath 108. A fluid may be introduced via the fluid input end 152 and discharged via the fluid output end 154, or vice versa. For example, the fluid may be introduced to the elongated flexible tube 110 by the fluid pump and fluid source 106. The fluid pump and fluid source 106 may fill the elongated flexible tube 110 (e.g., 110A-C) with a fluid such as saline or saline/contrast mixture. The fluid may be electrically conductive to support the generation of the shock waves. In some variations, the elongated flexible tube 110 may have one fluid end, through which the fluid may be introduced to the tube and discharged from the tube. For example, the fluid input end 152 and the fluid output end 154 may form one opening of the elongated flexible tube 110.

An elongated flexible tube 110 (e.g., tubes 110A-C) may comprise an inner wall and an outer wall. In some variations, the inner wall of the elongated flexible tube 110 may be heat treated such that the surface of the inner wall is smoother than a surface that is not heat-treated. A smoother inner wall may reduce the absorption of the shock wave generated by an electrode pair and therefore enhance the efficiency of delivering the shock wave to treat the calcium deposits in a heart valve. Moreover, a smoother surface may also reduce the resistance of circulating the fluid inside the elongated flexible tube 110. A smoother surface may also reduce air bubble forming and trapping, which can diminish the shock wave sonic output. A hydrophilic coating may eliminate or reduce this problem.

In some variations, the elongated flexible tube 110 may have a ring-shaped cross-section. For example, the inner wall of the elongated flexible tube 110 may form an inner cylinder to accommodate the wires, supporting wires, interleaved wire portions carrying electrode pairs, and the fluid. As an example, the inner diameter of the elongated flexible tube 110 may be ranging from about 0.04 inch to 0.08 inch; and the outer diameter of the elongated flexible tube 110 may be ranging from about 0.044 inch and about 0.088 inch; and the thickness of the wall of the elongated flexible tube 110 may be in the range of about 0.002 inch and about 0.02 inch. While increasing the wall thickness can improve strength, increasing the thickness of the wall of the elongated flexible tube 110 may also increase the absorption of energy generated by an electrode pair, thereby reducing the acoustic pressure and shear stress (induced by the acoustic pressure pulse) that are applied to the calcified deposits along the surface of cusps of a heart valve. It is appreciated that the elongated flexible tube 110 can have any desired cross-sectional shape and any desired dimensions for accommodate the components (e.g., wires, supporting wires, interleaved wire portions carrying electrode pairs, and the fluid) of a shock wave device for delivering the shock wave to treat the calcium deposits in a heart valve. In some variations, the material of the elongated flexible tube 110 may include nylon, rubber, plastic, aromatic polyurethane, and/or other materials having similar characteristics.

Figure 6:
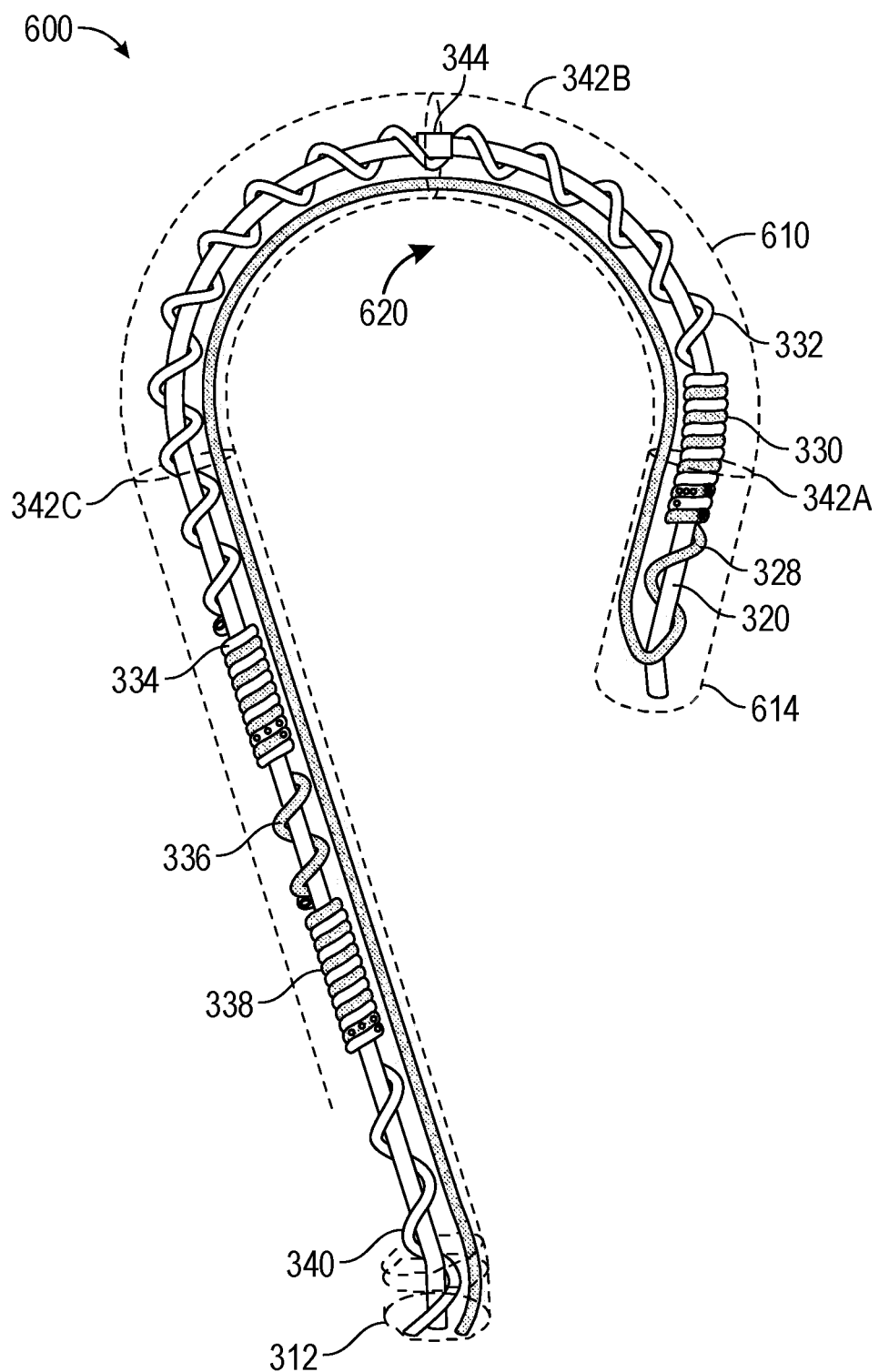
FIG. 6 depicts a schematic view of another exemplary elongated flexible tube and an array of electrode pairs associated with a plurality of wires disposed within the flexible tube.

As illustrated in FIGS. 1A-1B, in some variations, an elongated flexible tube 110 (e.g., 110A-C) may comprise a loop portion. The loop portion may be located near a distal end of the sheath 108. In some variations, the loop portion may comprise a horseshoe-shaped loop such that the two ends of the loop portion are neighboring to each other. In some variations, the loop portion may comprise a J-shaped loop (e.g., as shown in FIG. 6). The loop portion may be configured to be at least partially accommodated within a cusp of a heart valve to enable the shock waves to be delivered for softening and/or loosening and/or removing calcium deposits. One advantage of the tube design is that the electrode pairs can be positioned in closer proximity to a cusp of a heart valve than of some prior art balloon designs wherein the electrodes are mounted close to the center sheath and away from the balloon wall. As a result, the flexible tube comprising a loop portion may enhance the delivering of the shock wave to the calcium deposits. The treatment of calcium deposits in a heart valve is described in more detail below in connection with FIG. 2.

As shown in FIGS. 1A-1C, the loop portion of an elongated flexible tube 110 may comprise a plurality of wires and an array of interleaved wire portions carrying electrode pairs. For example, the elongated flexible tube 110A comprises a first wire 114, a first interleaved wire portion 116, a second wire 118, a second interleaved wire portion 120, a third wire 122, a third interleaved wire portion 124, and a fourth wire 126. An interleaved wire portion may comprise a plurality (e.g., 2) of portions of wires configured in an interleaved manner. For example, an interleaved wire portion may include a portion of a wire coiled with a portion of another wire. In some variations, the wires and interleaved wire portions are configured in series. For example, the first wire 114 may be electrically coupled to a positive terminal of a voltage source such as a high voltage pulse generator 102. The first interleaved wire portion 116 may comprise a portion of the first wire 114 interleaved with a first portion of the second wire 118. The first wire 114 may have an electrical voltage or potential that is more positive than the second wire 118. Similarly, the second interleaved wire portion 120 may comprise a second portion of the second wire 118 interleaved with a first portion of the third wire 122.

The second wire 118 may have an electrical voltage or potential that is more positive than that of the third wire 122. And the third interleaved wire portion 124 may comprise a second portion of the third wire 122 and a portion of the fourth wire 126. The third wire 122 may have an electrical voltage or potential that is more positive than that of the fourth wire 126. The fourth wire 126 may be electrically coupled to a negative terminal of a voltage source such as a high voltage pulse generator 102. While FIGS. 1A-1B illustrate three interleaved wire portions 116, 120, and 124, it is appreciated that an elongated flexible tube 110 may comprise any number of interleaved wire portions (e.g., two, three, four, five, six) in any desired configurations to deliver shock waves. For example, the elongated flexible tube 110A may comprises two interleaved wire portions (e.g., the first interleaved wire portion 116 and the second interleaved wire portion 120) coupled in series, but may not comprise the third interleaved wire portion 124 and the fourth wire 126. In this configuration, the third wire 122 may be electrically coupled to the negative terminal of a voltage source such as a high voltage pulse generator 102. In some variations, one or more interleaved wire portions may also be electrically coupled in parallel.

As will be discussed below with reference to FIGS. 3A-E, in the illustrated embodiment, each interleaved wire portion includes at least one pair of electrodes. Each electrode is defined by removing a small region of insulation from the wire. When a high voltage is delivered to the wires surrounded by a conductive fluid, an electrohydraulic discharge generates plasma that generates a shock wave at the arc-generating region. A conductive-fluid-filled tube may be pressurized at 2 ATM to 6 ATM.

In some variations, the high voltage pulse generator 102 can generate high voltage pulses in the range of about 1 kV-6 kV peak to peak. In one variation, the high voltage pulse generator 102 generates a voltage of about 5.0 kV and delivers the voltage to a plurality of interleaved wire portions (e.g., the first interleaved wire portion 116, the second interleaved wire portion 120, and the third interleaved wire portion 124) carrying an array of electrode pairs. The array of electrode pairs can be configured to generate shock waves in the conductive fluid in response to the voltage pulses generated by the voltage pulse generator 102, as described in more detail below.

As shown in FIGS. 1A-1C, in some variations, the wires and interleaved wire portions may be supported by support wire 160 disposed within the elongated flexible tube 110. The support wire 160 may be elongated and flexible. In some variations, the support wire 160 is non-conductive or metal with high dielectric insulator. Material of the support wire 160 can be polyimide coated Nitinol wire or similar property material. The support wire 160 may be in contact with the wires (e.g., the first wire 114, the second wire 118, the third wire 122, and the fourth wire 126) and the plurality of interleaved wire portions (e.g., the first, second, and third interleaved wire portions 116, 120, and 124). In one variation, the wires (e.g., 114, 118, 122, and 126) and the interleaved wire portions (e.g., 116, 120, and 124) may wrap around the support wire 160. In some variations, the support wire 160 extends substantially through the elongated flexible tube 110. One variation of the support wire 160 may comprise one or more layers of materials. For example, as shown in FIG. 1C, the outer layer 171 of the support wire 160 may comprise an electrical insulator material such as rubber, plastic, ceramics, and/or other materials having similar characteristics. The inner layer 172 of the support wire 160 may comprise an electrical conductor such as metal, alloy, nitinol, stainless steel, iron, copper, aluminum, lead, and/or other materials having similar characteristics. In some variations, the inner layer 172 may comprise memory materials such as memory alloys to remember the shape of the support wire 160 to reduce the burden of the practitioner to adjust the shape of the elongated flexible tube 110 each time it is inserted into the heart valve of the same patient.

Figure 2:
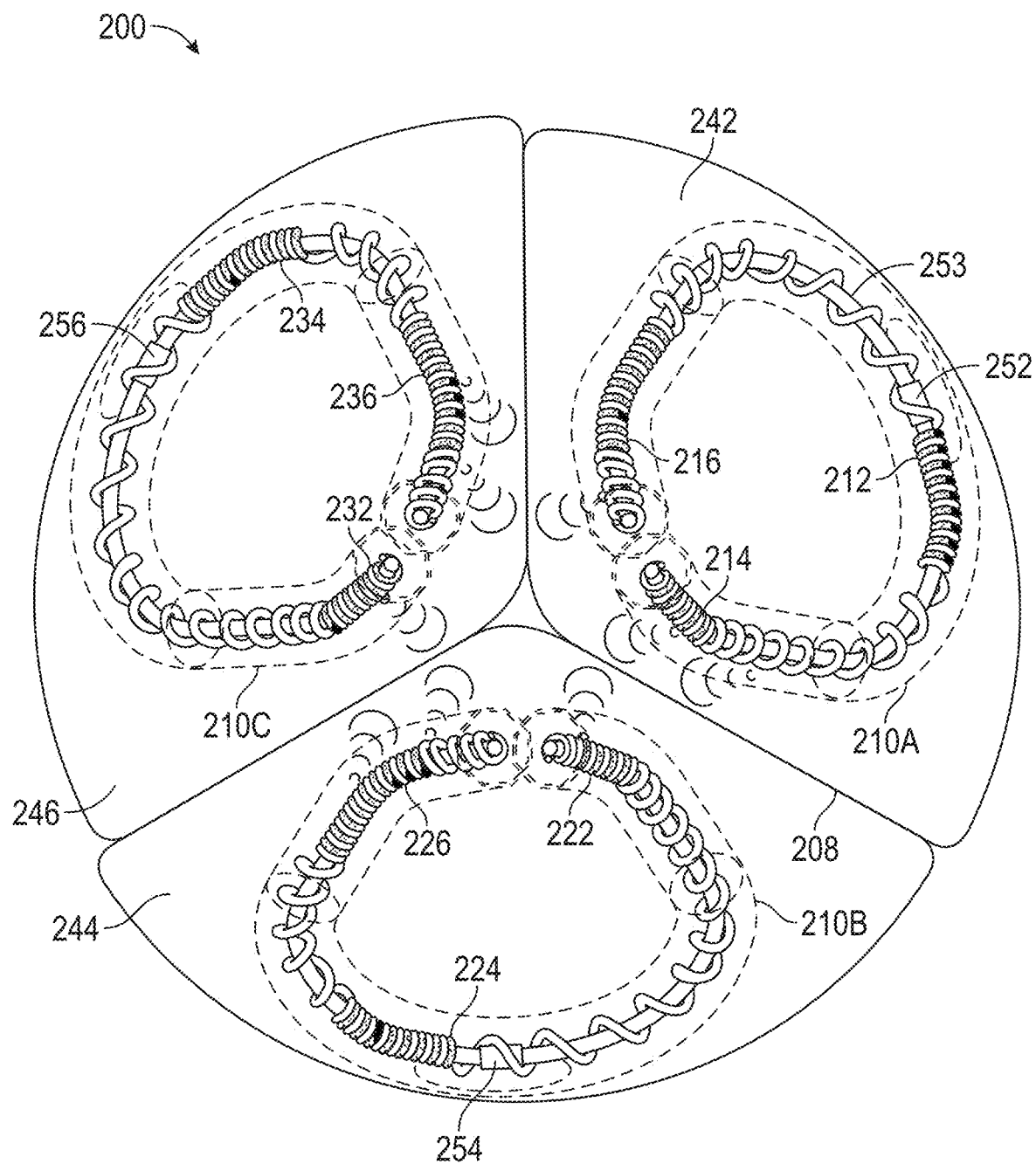
FIG. 2 depicts a schematic top view of elongated flexible tubes deployed in a heart valve.

FIG. 2 depicts a schematic top view of a shock wave device deployed in a heart valve 200. As described, in some variations, the shock wave device may comprise a plurality of elongated flexible tubes. For example, as shown in FIG. 2, the shock wave device comprises a first elongated flexible tube 210A, a second elongated flexible tube 210B, and a third elongated flexible tube 210C. The elongated flexible tubes 210A-C may each comprise two or more interleaved wire portions carrying electrode pairs. For example, as shown in FIG. 2, the elongated flexible tube 210A comprises interleaved wire portions 212, 214, and 216; the elongated flexible tube 210B comprises interleaved wire portions 222, 224, and 226; and the elongated flexible tube 210C comprises interleaved wire portions 232, 234, and 236. Each of the interleaved wire portions may carry a plurality of electrode pairs to generate shock waves.

In some variations, the elongated flexible tubes 210A-C may further comprise markers 252, 254, and 256, respectively. A marker may be disposed in the loop portion of the elongated flexible tube 210. For example, as shown in FIG. 2, the marker 252 is co-axially coupled to a support wire 253 supporting the interleaved wire portions 212, 214, and 216. Markers 254 and 256 may be similarly disposed. In some variations, markers 252, 254, and 256 may be radiopaque to allow a practitioner to identify the location, position, and/or orientation of the shock wave device as it is inserted through the vasculature of a patient. For example, the markers 252, 254, and 256 may be disposed proximal to the middle parts of the loop portions of elongated flexible tubes 210A-C, respectively. In some variations, one or more markers 252, 254, and 256 may be disposed proximal to one of the interleaved wire portions of elongated flexible tubes 210A-C, or disposed at any other location along the length of the elongated flexible tubes 210A-C. The markers 252, 254, and 256 may enable the practitioner to deploy the elongated flexible tubes 210A-C to a proper location. For example, using the markers 252, 254, and 256, the elongated flexible tubes 210A-C may be deployed to a location within concaved portion and/or sinus 242, 244, and 246 of the respective cusp of the heart valve 200. In some variations, the location of the elongated flexible tubes 210A-C may be determined based on fluoroscopy and/or ultrasound using the markers 252, 254, and 256. As a result, a space may be maintained between the tubes and the wall of the heart valve 200 to prevent obstruction of the openings to the coronary arteries.

As illustrated in FIG. 2, the interleaved wire portions (e.g., interleaved wire portions 212, 214, and 216) may be electrically coupled in series to a voltage source such as a high voltage pulse generator 102. After a practitioner confirms that the elongated flexible tubes 210A-C are located in their pre-determined or desired positions, one or more of the electrode pairs carried by the interleaved wire portions may be activated to produce shock waves. The location of the elongated flexible tubes 210A-C and their electrode pairs may be monitored throughout the treatment procedure as needed to confirm that the electrode pairs are in close proximity to and/or in contact with calcified regions of the wall of the heart valve 200.

As described in more detail below, the electrode pairs may generate shock waves, which apply acoustic pulses of energy that propagate through the conductive fluid filled in the elongated flexible tubes 210A-C. The acoustic pulses of energy generated from the electrode pairs (e.g., electrode pairs carried the by interleaved wire portions 214, 216, 222, 226, 232, and 236) may propagate through the conductive fluid to apply acoustic pressure and shear stress on calcified deposits along the surface of the cusp. As described, in some variations, the thickness of the wall of an elongated flexible tube (e.g., 210A-C) may affect the absorption of the energy generated by an electrode pair. For example, increasing the thickness of the wall of the elongated flexible tube 110 may increase the absorption of energy generated by an electrode pair, thereby reducing the acoustic pressure (and the induced stress associated with it) that is available to be applied to the calcified deposits along the surface of cusps of a heart valve. The thickness of the wall of the elongated flexible tube 110 may range from, for example, about 0.002 inch to 0.02 inch. In some variations, the surface of the elongated flexible tubes 210A-C may be heat treated such that it may be smoother than a surface that is not heat-treated. A smooth surface of elongated flexible tubes 210A-C reduces or eliminates cavities or roughness to allow the pulses of energy to propagate in all directions. Moreover, as a result of the smooth surface, some of the energy may be reflected and redirected to the calcified deposits, thereby enhancing the efficacy of the treatment. In some variations, the thickness of the wall of an elongated flexible tube (e.g., 210A-C) may be reduced when the surface of the wall is heat treated. A thinner wall may reduce the absorption of energy generated by an electrode pair. A thinner wall may also reduce the reflection of energy generated by an electrode pair. Thus, a thinner wall of an elongated flexible tube (e.g., 210A-C) may increase the pressure or stress that is available to be applied to the calcified deposits along the surface of cusps of a heart valve, thereby enhances the efficacy of the treatment. A heat treated surface may also reduce the absorption of the pulses of energy and thus reduce the stress applied on the elongated flexible tubes 210A-C, thereby enhancing the life time of the tubes.

As shown in FIG. 2, a plurality of shock waves may be applied to the cusps and/or other valve structures of the heart valve 200. In some variations, the location and/or orientation of the elongated flexible tubes 210A-C may be varied so that the energy from the shock waves may be positioned on different areas of a cusp. For example, shock wave treatment of a calcified cusp may comprise initiating shock waves from the electrode pairs carried by the interleaved wire portions 214 and 216 of elongated flexible tube 210A at a first location (which may, for example, apply mechanical forces to calcified deposits along a first edge of the cusp), then moving the elongated flexible tube 210A and/or the interleaved wire portions 214 and 216 to a second location, and then initiating shock waves from the electrode pairs carried by the interleaved wire portions 214 and 216 at the second location (which may, for example, apply the mechanical forces to calcified deposits along the second edge of the cusp). In some variations, the elongated flexible tubes 210A-C may accommodate multiple interleaved wire portions carrying electrode pairs (e.g., 3) that can be positioned to treat calcified deposits along multiple edges of the cusp in series or in parallel configurations, therefore reducing or eliminating the requirement of moving the elongated flexible tubes 210A-C and/or their respective electrode pairs. For example, as shown in FIG. 2, the shock waves can be generated from electrode pairs carried by interleaved wire portions 212, 214, and 216 electrically coupled in series to apply mechanical forces to calcified deposits along multiple (e.g., three) edges of the cusp. In some variations, the location and or/orientation of the electrode pairs inside the elongated flexible tubes 210 A-C may be varied so that the acoustic energy of the emitted shock waves may coherently interfere at a particular location causing a higher energy wave than the original emitted pulse. This can be achieved by geometrically aligning the electrode pairs and firing them at the same time so that the waves can create a focal region at a particular location near or at the calcified valve. Efficacy of the treatment may be subsequently evaluated based on imaging techniques (e.g., fluoroscopy and/or ultrasound) and/or physiological parameters. Examples of techniques that may be used to evaluate the efficacy of the treatment may include, but are not limited to, visual observation by ultrasound of leaflet activity (e.g., leaflet opening and closing) when the elongated flexible tubes 210A-C are withdrawn from the heart valve 200, measuring ejection fraction, Duke Activity Status Index (DASI), peak velocity, peak gradient, aortic valve area (AVA), Doppler velocity, etc. Optionally, after a desired amount of the calcium deposits have been cracked and/or loosened, and/or the leaflets of the heart valve have been softened, a transcatheter aortic valve implantation (TAVI) procedure may be performed. Cracking and/or breaking the calcium deposits on a heart valve may help to improve the outcome of a subsequent TAVI procedure. In some variations, a single cusp of the heart valve 200 may be treated at a time, while in other variations, two or more cusps of a valve may be treated in parallel. For example, as illustrated in FIG. 2, three cusps of the heart valve 200 may be treated in parallel with the three elongated flexible tubes 210A-C. Alternatively, three cusps of the heart valve 200 may be treated one after another using a single elongated flexible tube of a shock wave device. For people with bicuspid aortic valves, a shock wave device having two elongated flexible tubes may be used to treat the two cusps of the heart valve.

Figure 3A:
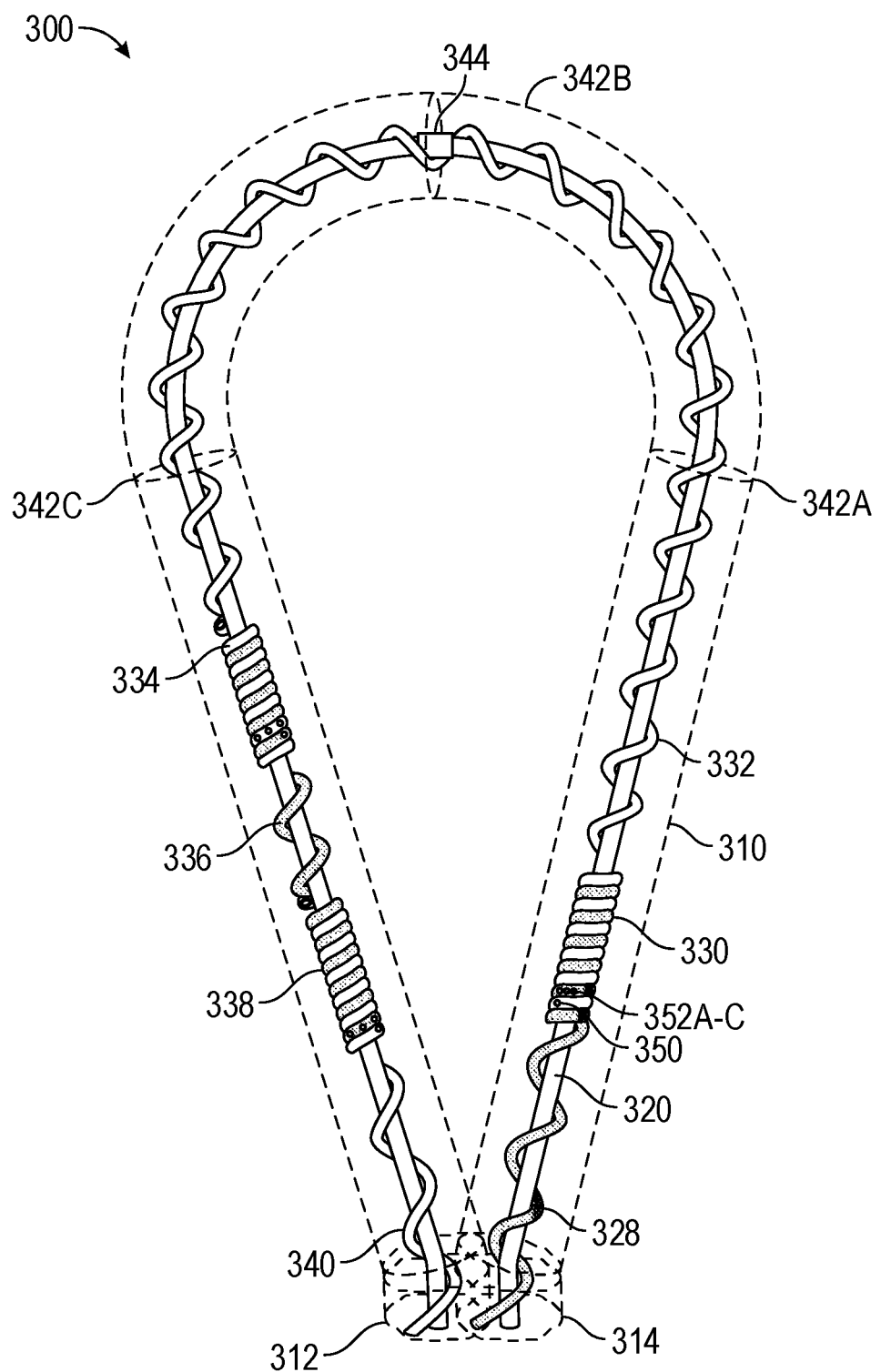
FIG. 3A depicts a schematic view of an exemplary elongated flexible tube and an array of electrode pairs associated with a plurality of wires disposed within the flexible tube.

FIG. 3A depicts a schematic view of an exemplary flexible tube 300 and an array of electrode pairs associated with a plurality of wires disposed within the flexible tube 300. As shown in FIG. 3A, an elongated flexible tube 310 may comprise a fluid input end 312, a fluid output end 314, a support wire 320, a first wire 340, a first interleaved wire portion 338, a second wire 336, a second interleaved wire portion 334, a third wire 332, a third interleaved wire portion 330, and a fourth wire 328. One variation of the wires 340, 336, and 332 may comprise a first layer surrounded by a second layer. The first layer may comprise conductive materials such as metal (e.g., copper), alloy, and/or other materials that are electrically conductive. The second layer may comprise insulator materials such as rubber, plastics, and/or other materials that are not electrically conductive. Similar to those described above, the first interleaved wire portion 338 may comprise a portion of the first wire 340 interleaved with a first portion of the second wire 336. The first wire 340 may be electrically coupled to a positive terminal of a voltage source and may have an electrical voltage or potential that is more positive than the second wire 336. Similarly, the second interleaved wire portion 334 may comprise a second portion of the second wire 336 interleaved with a first portion of the third wire 332. The second wire 336 may have an electrical voltage or potential that is more positive than that of the third wire 332. And the third interleaved wire portion 330 may comprise a second portion of the third wire 332 and a portion of the fourth wire 328. The third wire 332 may have an electrical voltage or potential that is more positive than that of the fourth wire 328. The fourth wire 328 may be electrically coupled to a negative terminal of a voltage source such as a high voltage pulse generator 102. It is appreciated that while in the above variation, the electrical voltage or potential decreases in the order of the first wire 340, the second wire 336, the third wire 332, and the fourth wire 328, the electrical voltage or potential of these wires may increase in the other variations (e.g., the fourth wire 328 has a higher voltage or potential than the third wire 332, which has a higher voltage or potential than the second wire 336, and so forth).

As shown in FIG. 3A, in some variations, the portion of the first wire 340 interleaves with the first portion of the second wire 336 to form a first coil. The first coil may have a center axis that is common to the portion of the first wire 340 and the first portion of the second wire 336. Similar, the second portion of the second wire 336 interleaves with the first portion of the third wire 332 to form a second coil. The second coil may have a center axis that is common to the second portion of the second wire 336 and the first portion of the third wire 332. And the second portion of the third wire 332 interleaves with a portion of the fourth wire 328 to form a third coil. The third coil may have a center axis that is common to the second portion of the third wire 332 and the portion of the fourth wire 328.

As shown in FIG. 3A, in some variations, the coils may comprise two portions of two different wires interleaved to each other in a manner that two neighboring wire portions in the coils are substantially parallel to each other. The two neighboring wire portions may have different electrical voltage or potential. As described in more details below, in a coil, two neighboring wire portions may carry an electrode pair, which comprise one or more arc-generating regions to generate shock waves. The energy associated with the shock waves may vary depending on the distance between the arc-generating regions of the two neighboring wire portions. For example, the shock wave generated may carry an increased energy with a reducing distance between the arc-generating regions the two neighboring wire portions. In some variations, the distance may be reduced to a certain threshold, as discussed in more detail below. In some variations, the location and or/orientation of the arc-generating regions may be varied so that the acoustic energy of the emitted shock waves may coherently interfere at a particular location causing a higher energy wave than the original emitted pulse. This can be achieved by geometrically aligning the arc-generating regions and firing them at the same time so that the waves can create a focal region at a particular location near or at the calcified valve.

As illustrated in FIG. 3A, in some variations, the shock wave device may comprise a plurality of spacers 342A-C. The spacers 342A-C may be configured to space the array of electrode pairs 330, 334, and 338 away from the inner wall of the elongated flexible tube 310. As described, the electrode pairs carried by interleaved wire portions 330, 334, and 338 may generate shock waves. The shock waves may apply mechanical forces on the inner wall of the elongated flexible tube 310. Some of the energy may be absorbed by the inner wall, which causes mechanical forces or stresses to be applied to the inner wall. The mechanical forces or stresses may increase as the distance between the electrode pairs carried by interleaved wire portions 330, 334, and 338 and the inner wall of the elongate flexible tube 310 reduces. The spacers 342A-C can keep the interleaved wire portions 330, 334, and 338 away from being in contact with the inner wall of the elongated flexible tube 310 to reduce or minimize the forces or stresses applied to the inner wall. As a result, the spacers 342A-C may enhance the life time of the elongated flexible tube 310. In some variations, the spacers 342A-C may include ring-shaped spacers and/or any other shaped spacers (e.g., oval-shaped).

Figure 3B:
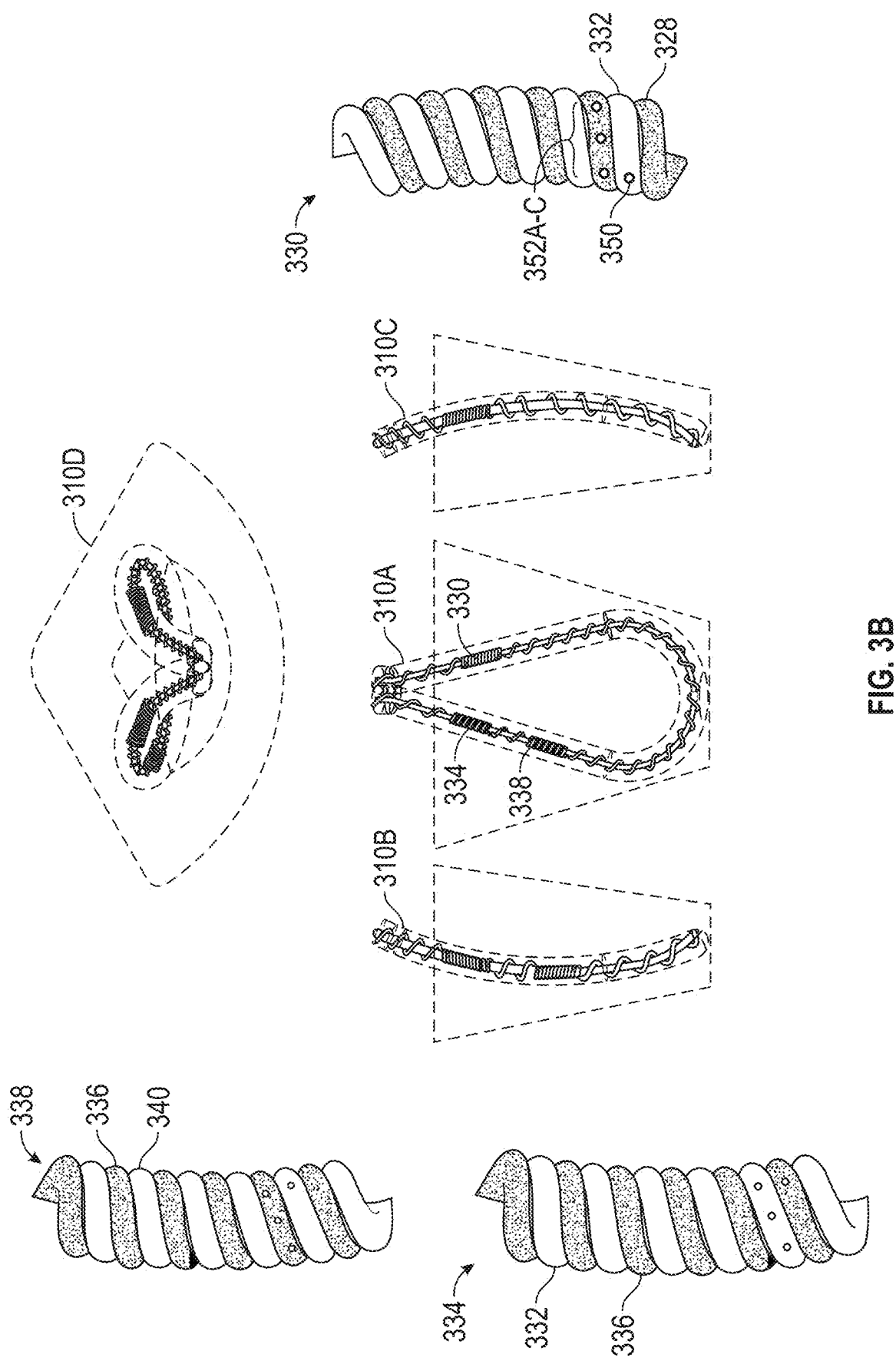
FIG. 3B depicts various views of an exemplary flexible tube and enlarged view of exemplary interleaved wire portions carrying the electrode pairs.
Figure 3C:
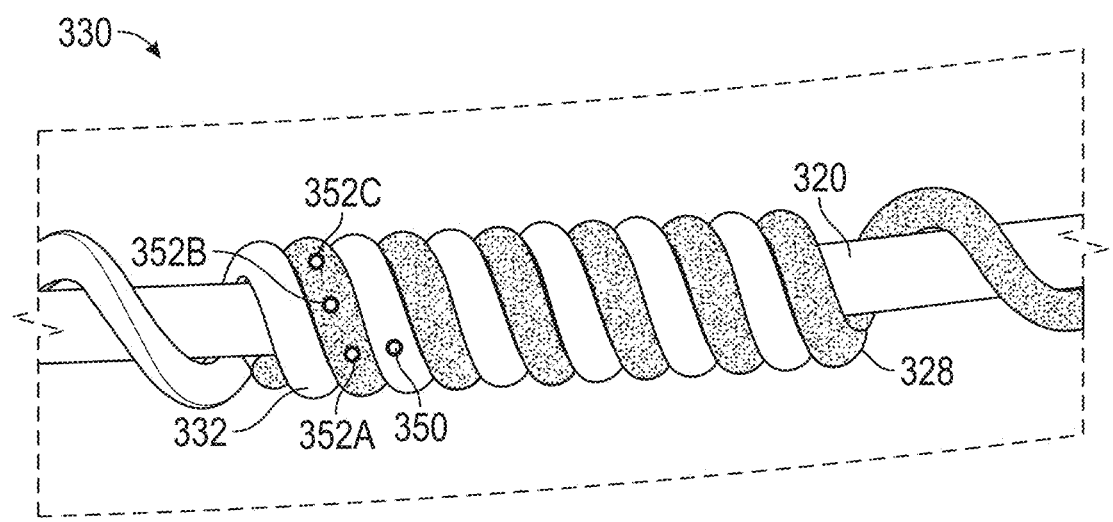
FIG. 3C depicts an enlarged view of an exemplary interleaved wire portion supported by a flexible support wire.

FIG. 3B depicts multiple views of an exemplary flexible tube and enlarged view of exemplary interleaved wire portions carrying electrode pairs. For example, FIG. 3B illustrates a front view 310A, side views 310B-C, and a top view 310D of the elongated flexible tube 310. FIG. 3B further depict enlarged views of exemplary interleaved wire portions 330, 334, and 338. FIG. 3C depicts an enlarged view of the interleaved wire portion 330 supported by a flexible support wire 320. As described, in some variations, an interleaved wire portion (e.g., interleaved wire portions 330, 334, and 338) may comprise two wire portions interleaved together to form a coil. The coil may comprise two portions of different wires interleaved to each other in a manner that two neighboring wire portions are substantially parallel to each other. In a coil, two neighboring wire portions may have different electrical voltages or potentials. In some variations, to generate shock waves, each of the two neighboring wire portions may comprise one or more arc-generating regions to form an electrode pair. For example, as shown in FIGS. 3B and 3C, the two neighboring portions of wires 328 and 332 in the interleaved wire portion 330 comprise one or more arc-generating regions 352A-C and 350, respectively. Similarly, the wire portions of interleaved wire portions 334 and 334 may also comprise one or more arc-generating regions. The neighboring arc-generating regions may form electrode pairs. For example, the arc-generating regions 350 and 352A-C form an electrode pair.

In some variations, the arc-generating regions may be devoid of insulation and may be configured to generate sparks (or plasma arcs) between two neighboring wire portions to convey the shock waves. As described, a wire (e.g., wire 328, 332, 336, and 340) may comprise a first layer that is electrically conductive and a second layer that is an electrical insulator. The first layer of a wire may be surrounded by the second layer. As shown in FIGS. 3B and 3C, in the arc-generating regions (e.g., regions 350 and 352A-C) of an electrode pair, the insulation of the wires is removed to expose the underlying electrically conductive layer. As described, in some variations, two neighboring wire portions in a coil may be configured to be substantially parallel to each other. In some variations, the arc-generating regions of two neighboring wire portions may be positioned to align with one another. For example, as shown in FIG. 3C, the arc-generating region 350 of the portion of wire 332 may be positioned to align with the arc-generating region 352A of the portion of wire 328. The alignment of arc-generating regions between two neighboring wire portions may improve the efficiency of spark generation (or plasma arc generation). For example, plasma arcs may be more easily generated between two closely positioned arc-generating regions. As described, in some variations, the distance between the two arc-generating regions may be reduced to a certain threshold associated with an optimum acoustic energy output. For example, in one variation of a single electrode pair system including two arc-generating regions, the distance between the two arc-generating regions may be reduced to about 0.2 mm (or about 0.008 inch). Further reducing the distance may reduce the acoustic energy output. In some variations where multiple electrode pairs in series are included in a shock wave device, the distance may be divided serially in several electrode gaps.

As shown in FIGS. 3B and 3C, in some variations, a wire portion that has a more positive electrical voltage or potential than the neighboring wire portion may comprise a smaller number of arc-generating regions. For example, in the interleaved wire portion 330, the portion of the wire 328 comprises at least two arc-generating regions 352A-C and the portion of the wire 332 comprises one arc-generating regions. As described above in connection with FIG. 3A, in one variation, in the interleaved wire portion 330, the portion of the wire 332 may have an electrical voltage or potential that is more positive than the portion of wire 328, and thus the portion of wire 332 may have a smaller number of arc-generating regions the portion of wire 328. As described in more detail below, the number of the arc-generating regions and/or the positions of the arc-generating regions may be configured to compensate spark-induced (or arc-induced) erosion of the insulation of one or both of the neighboring wire portions.

Similarly, as shown in FIG. 3B, in the interleaved wire portion 334, the portion of the wire 332 comprises at least two arc-generating regions and the portion of the wire 336 comprises one arc-generating regions. In the interleaved wire portion 334, the portion of the wire 336 may have an electrical voltage or potential that is more positive than the portion of the wire 332, and thus wire 336 may have a smaller number of arc-generating regions than the portion of wire 332. In the interleaved wire portion 338, the portion of the wire 336 comprises at least two arc-generating regions and the portion of the wire 340 comprises one arc-generating regions. In the interleaved wire portion 338, the portion of the wire 340 may have an electrical voltage or potential that is more positive than the portion of the wire 336, and thus the portion of the wire 340 may have a smaller number of arc-generating regions than the portion of wire 336.

Figure 3D:
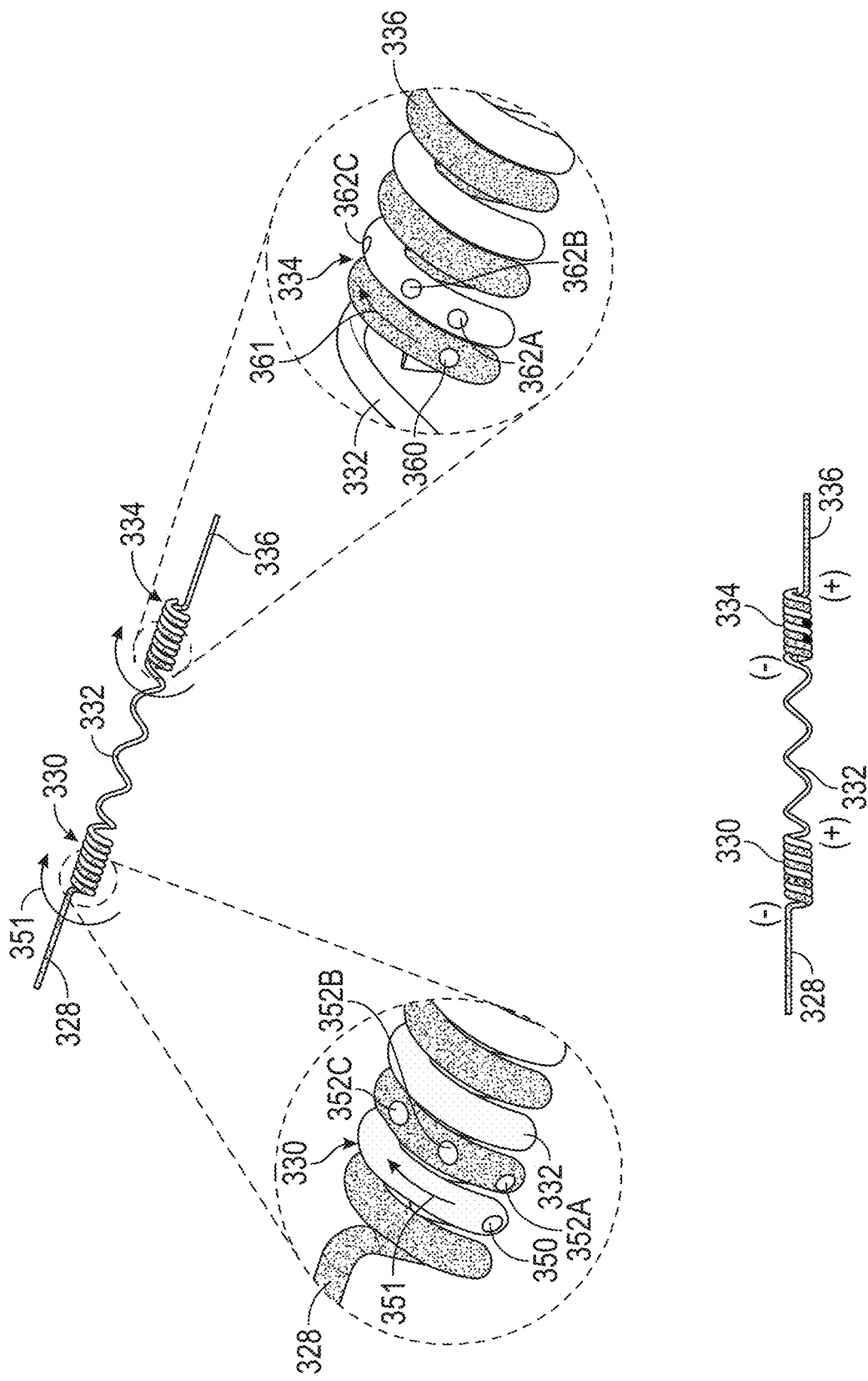
FIG. 3D depicts a schematic view of two neighboring interleaved wire portions in a coiled configuration and their enlarged view.
Figure 3E:
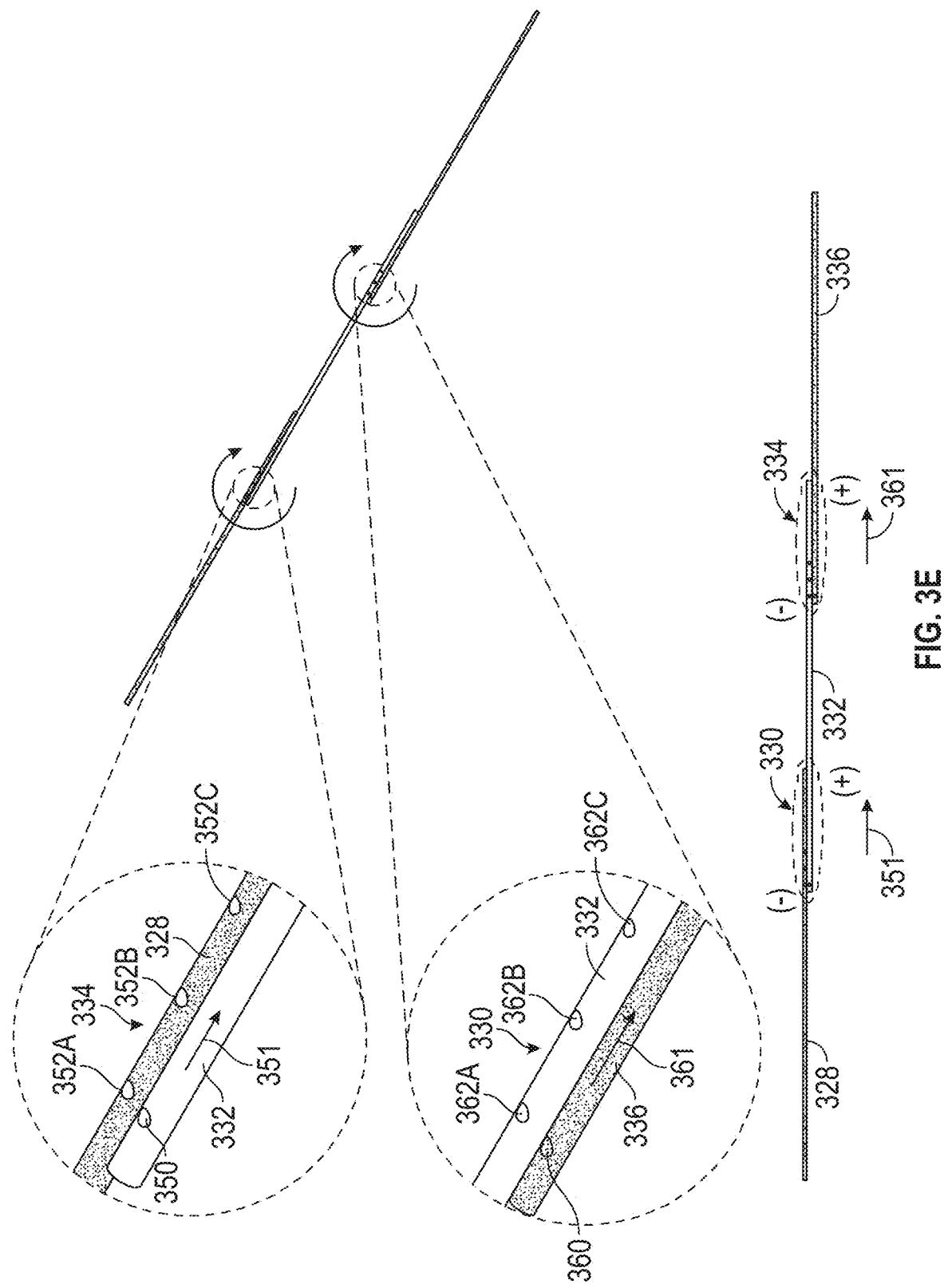
FIG. 3E depicts a schematic view of two neighboring interleaved wire portions with the coils straightened and their enlarged view.

FIG. 3D depicts a schematic view of two neighboring interleaved wire portions in a coiled configuration and their enlarged view. FIG. 3E depicts a schematic view of two neighboring interleaved wire portions with the coils straightened and their enlarged view. FIGS. 3D and 3E are described together. FIGS. 3D and 3E illustrate the interleaved wire portions 330 and 334. As described, the interleaved wire portion 330 may comprise a portion of the wire 328 interleaved (e.g., coiled) with a portion of wire 332. In one variation, the wire 328 may have a voltage or potential that is more negative than the wire 332. For example, the wire 328 may be electrically coupled to a negative terminal of a voltage source. In the interleaved wire portion 330, the portion of the wire 328 and the portion of the wire 332 may comprise one or more arc-generating regions configured to form an electrode pair. For example, in the interleaved wire portion 330, the portion of the wire 328 may include a plurality of arc-generating regions 352A-C and the portion of the wire 332 may include one arc-generating region 350. Arc-generating regions 350 and 352A-C form an electrode pair. As described, the arc-generating regions may be devoid of insulation for inducing electrical sparks (or plasma arcs) between the two arc-generating regions that have different voltages or potentials. For example, initially, plasma arcs may be generated between two neighboring arc-generating regions 350 and 352A, because the wire 328 has a voltage or potential that is more negative than the wire 332.

In some variations, plasma arcs may cause erosion of the insulation of the wires. Erosion may occur in the direction corresponding to the direction of increasing voltage or potential. For example, as shown in FIGS. 3D and 3E, in the portion of the wire 332 of interleaved wire portion 330, the voltage or potential may increase in the direction indicated by an arrow 351. Thus, the insulation erosion of the portion of the wire 332 may initiate from the arc-generating region 350 and propagate in the direction indicated by the arrow 351. In some variations, the arc-generating region in two neighboring wire portions may be positioned to compensate the arc-induced erosion of the insulation of one or more of the wire portions. For example, as shown in FIGS. 3D and 3E, in the interleaved wire portion 330, the arc-generating region 350 and the arc-generating region 352A may be positioned to align with each other to initiate the spark generation (or plasma arc generation). In the interleaved wire portion 330, one or more additional arc-generating regions 352B-C in the portion of wire 328 may be positioned corresponding to the erosion direction in the portion of the wire 332, such that as the insulation erosion of the portion of the wire 332 propagate in the direction indicated by the arrow 351, plasma arcs may be generated between the one or more addition arc-generating regions 352B-C and the eroded portion of the wire 332. It is appreciated that one or more additional arc-generating regions may be positioned corresponding to the erosion direction in the portion of the wire 332. Positioning the arc-generating regions in such a manner may increase the efficiency of spark/plasma arc generation, improve the consistency and continuity of the shock waves, and enhance the lifetime of the shock wave device.

In some variations, plasma arcs may cause erosion of the insulation of the wires. Erosion may occur in the direction corresponding to the direction of increasing voltage or potential. In order to reduce the bias of erosion, in some variations, a shock wave device with polarity switching may be used with a regular electrode configuration (similar to those described in co-pending U.S. patent application Ser. No. 15/138,147, filed Apr. 25, 2016, which is incorporated by reference in its entirety) to even the directional erosion mentioned above. Thus, the insulation erosion of the portion of the wire 332, as shown in FIGS. 3D and 3E, may initiate from the arc-generating region 350 and propagate in the direction indicated by the arrow 351, and in the next pulse or subsequent number of pulses, may propagate in the direction opposite to that one in the arrow 351, allowing erosion to act evenly on both sides and preventing the electrode gap from continuing to wear in an even fashion (as described in more detail in U.S. patent application Ser. No. 15/138,147, filed Apr. 25, 2016).

As illustrated in FIGS. 3D and 3E, similarly, in the portion of the wire 336 of the interleaved wire portion 334, the voltage or potential increases in the direction indicated by an arrow 361. Thus, the insulation erosion of the portion of the wire 336 may initiate from the arc-generating region 360 and propagate in the direction indicated by the arrow 361. As described, the arc-generating regions in two neighboring wire portions may be positioned to compensate the arc-induced erosion of the insulation of one or more of the wire portions. For example, as shown in FIGS. 3D and 3E, in the interleaved wire portion 334, the arc-generating region 360 and the arc-generating region 362A may be positioned to align with each other to initiate the spark generation. In the interleaved wire portion 334, one or more additional arc-generating regions 362B-C in the portion of the wire 332 may be positioned corresponding to the erosion direction in the portion of the wire 336, such that plasma arcs may be generated between the one or more addition arc-generating regions 362B-C and the eroded portion of the wire 336. As discussed above, there may be any number (e.g., two, three, four, five, six) of electrode pairs carried by the interleaved wire portions within a single elongated flexible tube.

Figure 4:
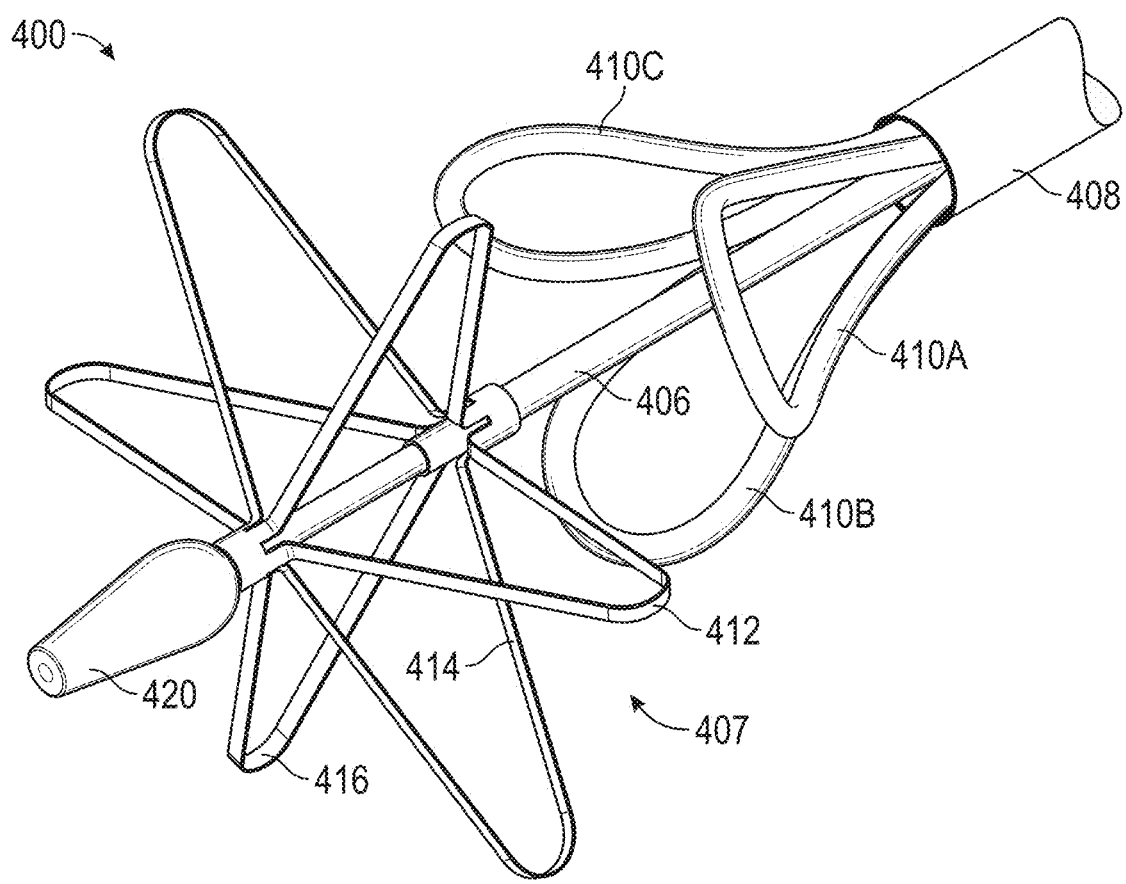
FIG. 4 depicts a prospective view of one variation of a self-expanding anchor that may be used with a shock wave device.

In some variations, the shock wave device may comprise a self-expanding anchor, which may be expanded automatically after the anchor is deployed. FIG. 4 depicts a prospective view of one variation of a self-expanding anchor that may be used with a shock wave device. As shown in FIG. 4, a shock wave device 400 may comprise a sheath 408, a plurality of elongated flexible tubes 410A-C, a shaft 406, and an anchor 407. The sheath 408 and plurality of elongated flexible tube 410A-C are similar to those described above. The anchor 407 may comprise a self-expanding scaffold 414. Optionally, the device 400 may comprise an atraumatic tip 420 located at the distal end of the shaft 406. The scaffold 414 may comprise one or more closed-form structures, such as lobes (or arms) 416. The arms 416 may be arranged in a radial symmetric configuration around the shaft 406, or in other variations, may be arranged in a non-symmetric configuration. The anchor 407 may comprise shape-memory material such as nickel-titanium alloy. In some variations, the anchor 407 may be a central anchor extending between and beyond the ends of the elongated flexible tubes 410A-C and configured to pass through the leaflets of the heart valves and into the ventricle to stabilize the position of the sheath 408. For example, the anchor 407 may be pushed through the valve orifice, expanded, and then pulled up against the heart valve leaflets to help further engage or contact the shock wave electrode pairs with the leaflets and/or cusps. The anchor 407 is similar to the anchor described in more detail in co-pending U.S. patent application Ser. No. 14/940,029 filed Nov. 12, 2015 (U.S. Pat. App. Publication 2016/0135828), which is hereby incorporated by reference in its entirety.

Figure 5:
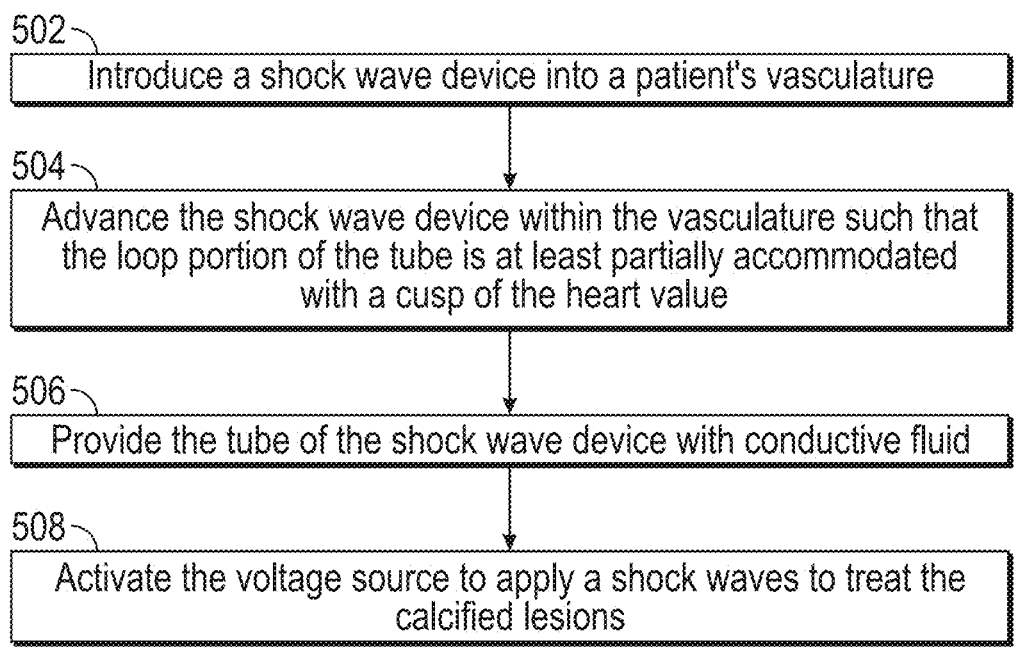
FIG. 5 is a flowchart representation of a method for delivering shock waves to treat calcified lesions in a heart valve.

FIG. 5 is a flowchart representation of a method for delivering shock waves to treat calcified lesions in a heart valve. In some methods, such as is depicted in FIG. 5, a shock wave device may be introduced (502) into a patient's vasculature. The shock wave device may comprise one or more elongated flexible tubes (e.g., 3). In some variations, the elongated flexible tube may be carried by a sheath and may have a fluid input end. The fluid input end of the tube may be located near a proximal end of the sheath. The tube may include a loop portion located near a distal end of the sheath. The loop portion may be configured to be at least partially accommodated within a cusp of the heart valve. The tube may be fillable with a conductive fluid via the fluid input end of the tube. The shock wave device may further comprise an array of electrode pairs associated with a plurality of wires positioned within the loop portion. The electrode pairs may be electrically connectable to a voltage source and configured to generate shock waves in the conductive fluid in response to voltage pulses.

In some variations, the shock wave device may be advanced (504) within the vasculature such that the loop portion of the tube is at least partially accommodated with a cusp of the heart valve. The tube of the shock wave device may be provided (506) with conductive fluid. As described, the conductive fluid may be provided from a fluid source using a fluid pump. The voltage source may be activated (508) to apply shock waves to treat the calcified lesions of the heart valve. As described, using one or more elongated flexible tubes, one or more cusps of a heart valve may be treated in serial or in parallel.

FIG. 6 depicts a schematic view of another exemplary flexible tube 600 and an array of electrode pairs associated with a plurality of wires disposed within the flexible tube 600. As shown in FIG. 6, flexible tube 600 may comprise an elongated flexible tube 610 that includes a J-shaped curved portion 620 instead of a horseshoe-shaped loop portion of elongated flexible tube 310. The J-shaped curved portion 620 may be configured to be at least partially accommodated within a cusp of the heart valve.

In some variations, the elongated flexible tube 600 may comprise a fluid input end 312, a support wire 320, a first wire 340, a first interleaved wire portion 338, a second wire 336, a second interleaved wire portion 334, a third wire 332, a third interleaved wire portion 330, and a fourth wire 328. As depicted in FIG. 6, an array of three electrode pairs is disposed within the tube 610. The first electrode pair is associated with a portion of the first wire 340 and a portion of the second wire 336 interleaved in a coiled configuration, with the first wire having an electrical potential that is more positive than that of the second wire. The second electrode pair is associated with a portion of the second wire 336 and a portion of the third wire 332 interleaved in a coiled configuration, with the second wire having an electrical potential that is more positive than that of the third wire. The third electrode pair is associated with a portion of the third wire 332 and a portion of the fourth wire 328 interleaved in a coiled configuration, with the third wire having an electrical potential that is more positive than that of the fourth wire. These components are similar to those described above in connection with FIG. 3A and are thus not repeatedly described.

In some variations, the distal end of the elongated flexible tube 600 (e.g., end 614) may be sealed such that the conducive fluid flows in and out through the open proximal end of the elongated flexible tube 610 (e.g., fluid input end 312). Moreover, a wire associated with the electrode pair closest to the distal end of the tube is configured to extend at least from the sealed distal end of the tube to the open proximal end of the tube. As illustrated in FIG. 6, because the end 614 is sealed, a portion of the fourth wire 328 may be configured to return to the fluid input end 312 to electrically couple to a negative terminal of a voltage source such as a high voltage pulse generator 102. In other words, the fourth wire, which is associated with the electrode pair closest to the distal end of the tube, is configured to extend at least from the sealed distal end of the tube to the open proximal end of the tube. In some variations, the portion of the fourth wire 328 that returns to the fluid input end 312 may be configured to be positioned away from the electrode pairs of the interleaved wire portions (e.g., wire portions 330, 334, and 338) such that it does not interfere with the shock wave generated by the electrode pairs. For example, the portion of the fourth wire 328 that returns to the fluid input end 312 may be configured to be positioned in the opposite side from the side of the arc-generating regions of the interleaved wire portions 338, 334, and 330. In some variations, the elongated flexible tube 600 comprising a J-shaped curved portion may have a smaller dimension (e.g., length) than the elongated flexible tube 310 comprising a horseshoe-shaped loop portion. Smaller dimension may enable the shock wave device to be advanced more easily within the vasculature.

As discussed above, to maintain the maximum shockwave output, it would be desirable to remove debris and air bubbles from the tube and replenish the tube with fresh conductive fluid. For a tube having a horseshoe-shaped loop portion, a pressure relief valve may be attached to the fluid output end so the pump can deliver the conductive fluid at a constant pressure; additionally or alternatively, a pressure regulator may be attached at the fluid input end. For a tube having a sealed distal end such as a tube having a J-shaped loop portion (e.g., the elongated flexible tube 610) or a tube having a straight configuration (e.g., the elongated flexible tube 710), the elongated flexible tube may include an output port at the proximal end of the tube such that the fluid makes a U-turn through the separated lumen. In some examples, if the support wire is a nitinol tube, the nitinol tube can be used to flush the elongated flexible tube with fresh fluid, which enters the elongated flexible tube via the distal end of the nitinol tube. Suction may be applied at the output port at the proximal end of the elongated flexible tube to increase the outward flow of the fluid.

Figure 8:
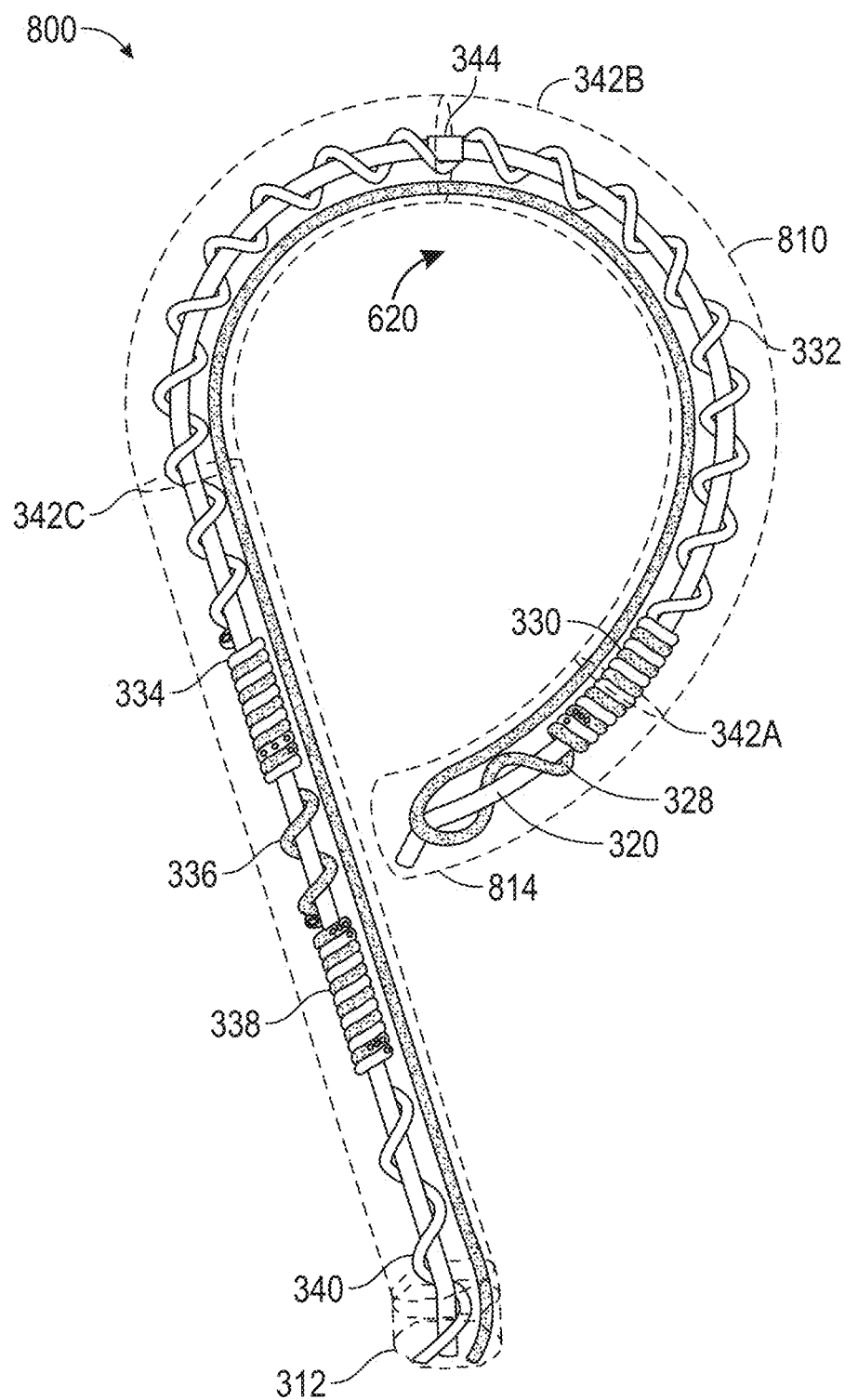
FIG. 8 depicts a schematic view of another exemplary elongated flexible tube and an array of electrode pairs associated with a plurality of wires disposed within the flexible tube.

In some variations, when the elongated flexible tube 610 is being deployed via a sheath, the J-shaped curved portion is straightened out (i.e., the distal end of the elongated flexible tube is unfolded and is substantially straight against the wall of the sheath). During deployment, when the elongated flexible tube 610 is extended out of the sheath, the distal end of the elongated flexible tube is configured to curl into a loop-like shape to prevent the sealed distal end of the tube from lodging in the ostium of a coronary artery. FIG. 8 depicts a schematic view of the exemplary flexible tube 610 in an exemplary deployment configuration (i.e., after the tube is extended out of the sheath and before the tube is filled with a fluid). In this deployment configuration, the flexible tube 610 includes a loop portion located near a distal end of the sheath. In some variations, the shape of the loop portion may be set by the support wire. The loop portion of the elongated flexible tube 610 is configured to partially unfold when the tube is filled with a pressurized conductive fluid via the open proximal end of the tube. Thus, after the loop portion is deployed safely into the cusp, the tube 610 is inflated with the pressurized conductive fluid, which causes the loop portion to partially unfold and take on a U shape. In other words, during deployment, the curve of the distal end of the tube (depicted in FIG. 8) is more closed than the curve of the distal end in the operating configuration (depicted in FIG. 6).

Figure 9C:
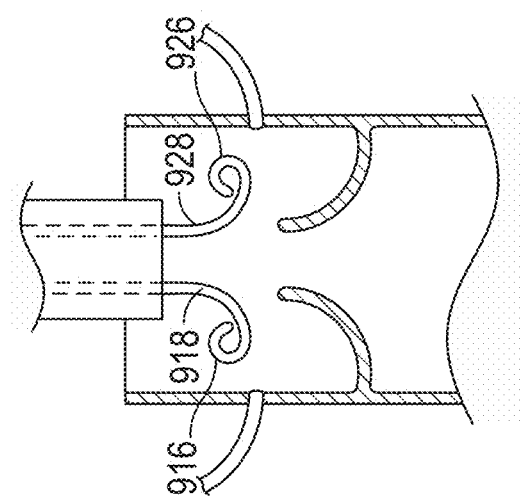
FIG. 9C depicts another step of the exemplary method for treating a calcified heart valve using a shock wave device.
Figure 9B:
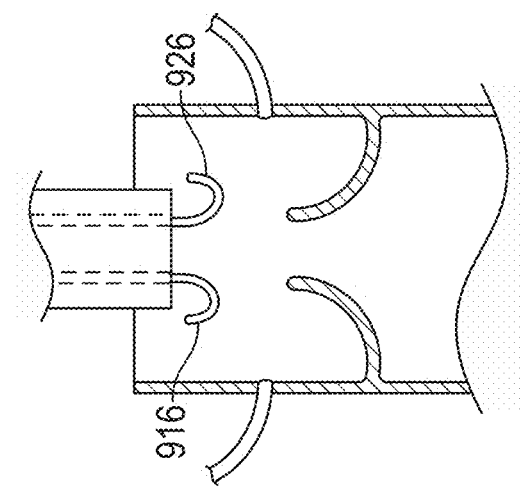
FIG. 9B depicts another step of the exemplary method for treating a calcified heart valve using a shock wave device.
Figure 9A:
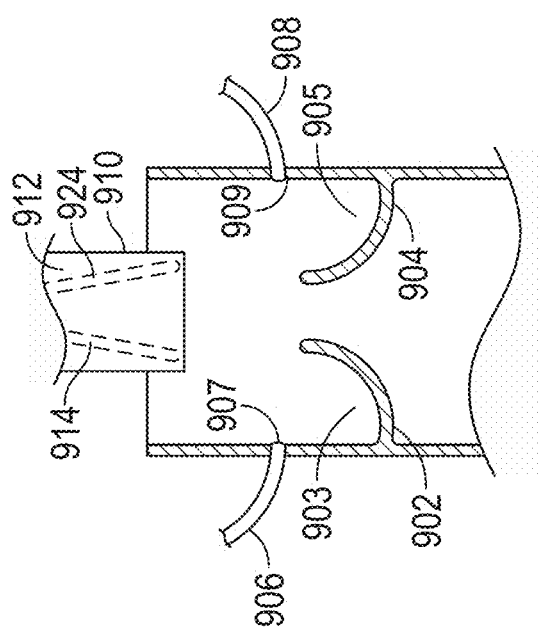
FIG. 9A depicts a step of an exemplary method for treating a calcified heart valve using a shock wave device.

FIGS. 9A-9D depict an exemplary method for treating a calcified heart valve (e.g., an aortic valve) using a shock wave device such as the one depicted in FIG. 8. Although the method depicted there uses a shock wave device comprising two elongated flexible tubes, it should be understood that this method may be performed using a shock wave device comprising one or three elongated flexible tube(s). FIG. 9A depicts a cross-sectional schematic view of an aortic valve with the left cusp 902 and the right cusp 904 (the posterior cusp is not shown for the sake of simplicity). The concave portion 903 of the left cusp 902 includes the opening 907 of the left coronary artery 906. The concave portion 905 of the right cusp 904 includes the opening 909 of the right coronary artery 908. A sheath 910 may be introduced into the vasculature and advanced in a retrograde direction (e.g., via a femoral artery) to the aortic valve. The sheath 910 (as well as any of components of the shock wave device) may comprise a radiopaque band or marker so that the location of the sheath may be determined using fluoroscopy. Alternatively or additionally, the location of the sheath and/or any shock wave devices may be determined using ultrasound. The distal end of the sheath 910 may be positioned close to but spaced from the cusps of the heart valve. A shock wave device 912 may then be advanced through the sheath 910 to the aortic valve. The shock wave device 912 may comprise a first elongated flexible tube 914 and a second elongated flexible tube 924.

As depicted in FIG. 9A, both elongated flexible tubes 914 and 924 are straightened out within the sheath. Specifically, the distal end of the first elongated flexible tube 914 and the distal end of the second elongated flexible tube 924 are both unfolded and maintain substantially straight against the wall of the sheath. The straight shape allows the elongated flexible tubes to be carried within a sheath having a smaller diameter. The distal ends of the tubes are biased (or prebent) such that they will curl into loops when extended out of the sheath.

As depicted in FIG. 9B, when the elongated flexible tubes 914 and 924 are extended out of the sheath 910, both distal ends of the tubes start to curl into their prebent/deployment shape (i.e., loops). As depicted in FIG. 9C, the distal end of the elongated flexible tube 914 curls into a loop portion 916 and the distal end of the second elongated flexible tube 924 curls into a loop portion 926. As discussed above with respect to FIG. 8, the loop portions are configured to partially unfold when the corresponding tubes are filled with a pressurized conductive fluid.

In some variations, the shaft portions above the loop portions of the elongated tubes may be biased such that they bend at an angle. As depicted in FIG. 9A, the shock wave device 912 may be advanced through the sheath 910 in a compressed configuration, where the shaft portions of the first and second elongated flexible tubes are generally aligned with the longitudinal axis of the sheath 910. In contrast, as depicted in FIG. 9C, extending the shock wave device 912 distally beyond the distal end of the sheath may allow the shaft portions 918 and 928 to assume their bent configuration, thereby expanding the shock wave device such that the first and second loop portions 916, 926 (deflated during delivery) contact the aortic valve wall.

Figure 9E:
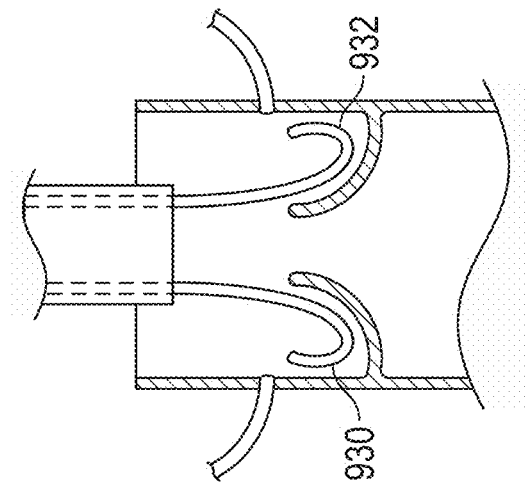
FIG. 9E depicts another step of the exemplary method for treating a calcified heart valve using a shock wave device.
Figure 9D:
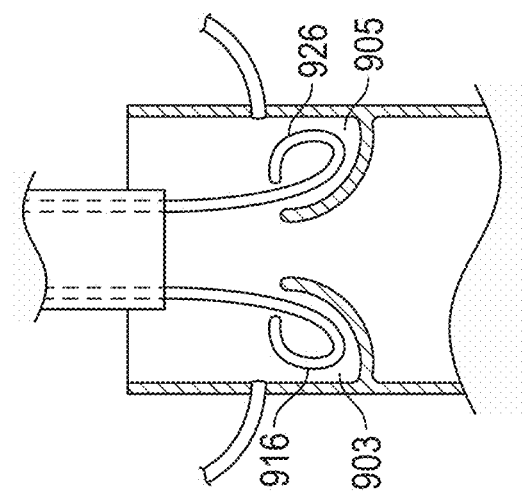
FIG. 9D depicts another step of the exemplary method for treating a calcified heart valve using a shock wave device.

As depicted in FIG. 9D, the expansion of the shock wave device may at least partially align the loop portions with the concave portions 903, 905 of the left and right cusps. As such, the loop portions 916 and 926 of the tubes are at least partially accommodated within the cusps of the heart valve.

Next, as depicted in FIG. 9E, one or both of the loop portions may be filled with a pressurized conductive fluid via the open proximal ends of the tubes. The fluid causes each of the loop portions 916 and 926 to partially unfold into curved portions 930 and 932, respectively. The curved portions 930 and 932 self-align within the concave portions of the cusps. In some variations, only one tube may be inflated at a time, or two tubes may be inflated simultaneously. Inflating fewer tubes than the number of cusps of a valve may allow blood to flow through at least a portion of the valve, which may help to reduce the risk of an ischemic incident during the procedure.

After a practitioner confirms that the curved portions of the tubes are located in the desired position, one or more of the electrode pairs in the tubes may be activated to produce shock waves. The mechanical force from the shock waves may propagate through the conductive fluid to apply a mechanical force on any calcified deposit along the surface of the cusps. In some methods, a single cusp of a valve may be treated at a time, while in other methods, two or more cusps of a valve may be treated simultaneously.

Figure 10:
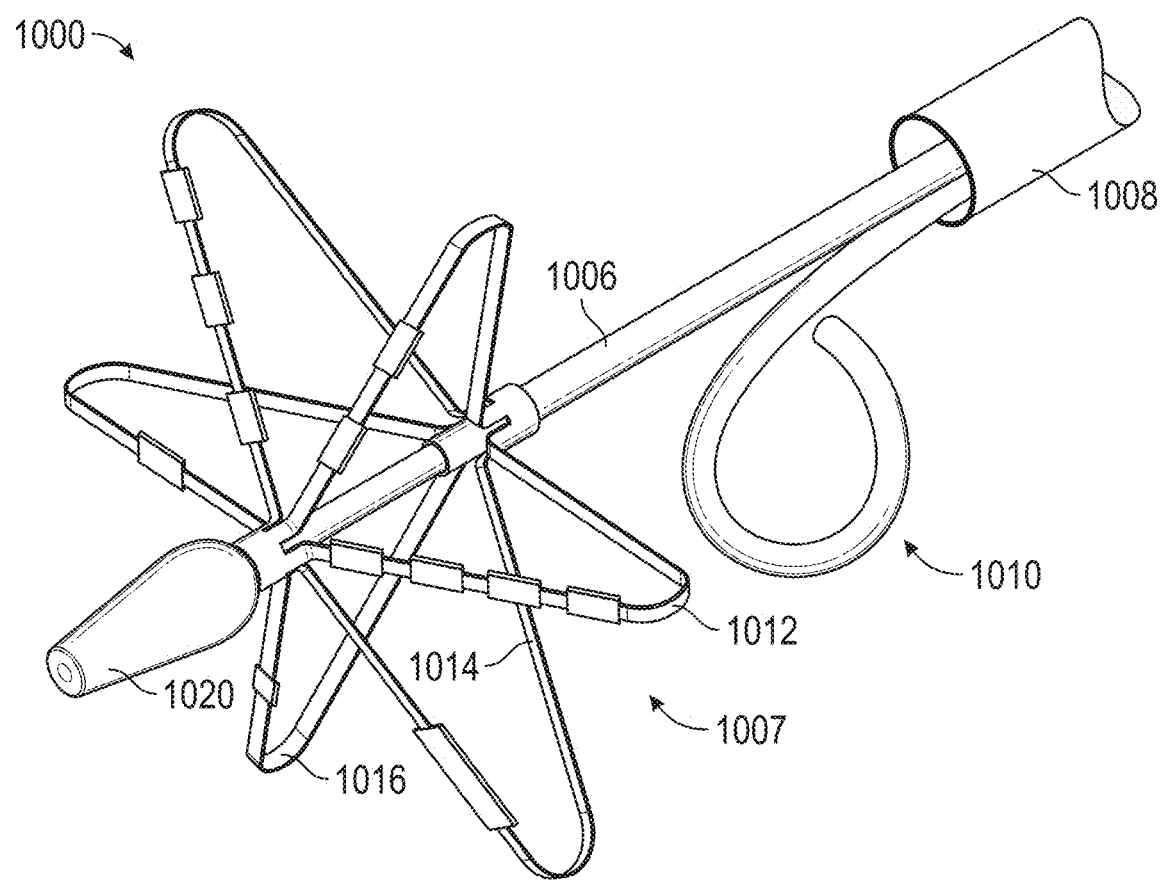
FIG. 10 depicts a prospective view of one variation of a self-expanding anchor that may be used with a shock wave device.

FIG. 10 depicts a prospective view of one variation of a self-expanding anchor that may be used with a shock wave device. As shown in FIG. 10, a shock wave device 1000 may comprise a single elongated flexible tube 1010, a sheath 1008, a shaft 1006, and an anchor 1007. The single elongated flexible tube 1010 is similar to the elongated flexible tube 610 in FIG. 6 and/or any of the tubes 914 and 924 in FIG. 9A. The components of the device 1000 are arranged to operate in a similar manner as described above with respect to the shock wave device 400 in FIG. 4. As depicted in FIG. 10, the central anchor 1007 may extend beyond the sealed distal end of the tube 1010 and can be configured to pass through the leaflets of the heart valves and into the ventricle to stabilize the position of the sheath.

The central anchor 1007 includes a plurality of arms 1012, 1014, 1016, 1018, 1022, and 1024. One or more markers may be disposed in a unique configuration on each of the plurality of arms such that the location of each arm can be identified during a procedure. The markers may include marker bands wrapped around the arms, markers glued on or crimped onto the arms, or a combination thereof. The configurations of marker(s) on two given arms may be different in marker count, marker shape, marker length, marker arrangement on the arm, or a combination thereof. In the depicted example, a first configuration corresponding to arm 1012 includes a series of four markers arranged in a linear fashion, whereas the second configuration corresponding to arm 1014 includes a single marker that is longer than any of four markers on the first arm 1012.

In some variations, the different marker configurations on the arms of the central anchor 1007 help a practitioner to identify the locations/positions/orientations of the arms and to navigate the elongated tube(s) of the shock wave device (e.g., the single elongated flexible tube 1010) from one cusp to another during a procedure. In an exemplary procedure, the shock wave device 1000 is introduced into a patient's vasculature and advanced within the vasculature such that the central anchor 1007 is placed into the ventricle. Specifically, the anchor 1007 may be pushed through the valve orifice, expanded, and then pulled up against the heart valve leaflets to help further engage or contact the shock wave electrode pairs with the leaflets and/or cusps. Based on the marker configurations, the locations of the arms are determined. In some variations, the locations of the arms may be determined based on fluoroscopy and/or ultrasound using the markers configurations. For example, upon identifying a configuration including a series of four markers of a certain length based on fluoroscopy, the practitioner can determine the location of the arm 1012.

Based on the locations of the arms determined based on the marker configurations, the tube 1010 is deployed and positioned such that the distal end of the tube (e.g., the loop portion) is at least partially accommodated with a first cusp of the heart valve. The first cusp of the heart valve may be in proximity to a particular arm of the central anchor. As such, the tube 1010 is positioned in proximity to the particular arm based on the determined location of the particular arm. In some variations, the tube 1010 is filled with a pressurized conductive fluid such that the loop portion partially unfolds into a less curved portion, as discussed above with respect to FIGS. 9A-D. After a practitioner confirms that the curved portion of the tube is located in the desired position, one or more of the electrode pairs in the tubes may be activated to produce shock waves to treat the calcified lesions. Efficacy of the treatment for the first cusp may be subsequently evaluated based on imaging techniques (e.g., fluoroscopy and/or ultrasound) and/or physiological parameters.

After treating the first cusp, the tube may be repositioned based on the determined locations of the arms of the central anchor such that the distal end of the tube is at least partially accommodated with a second cusp of the heart valve. Steps as described above are repeated such that the curved portion of the tube is located in the desired position, and the voltage source is activated to apply shock waves to treat the calcified lesions. It should be appreciated that the above-described method can be applied using any type of elongated flexible tube described herein.

Figure 7:
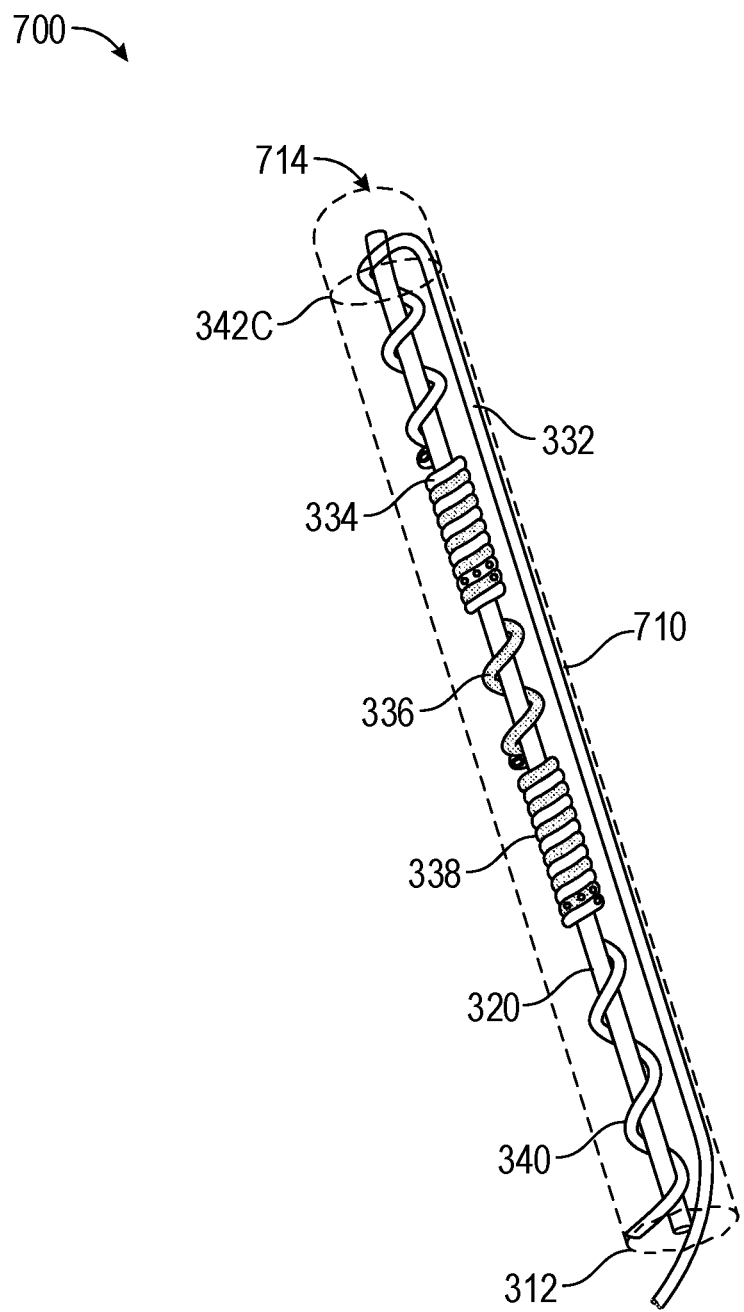
FIG. 7 depicts a schematic view of another exemplary elongated flexible tube and an array of electrode pairs associated with a plurality of wires disposed within the flexible tube.

FIG. 7 depicts a schematic view of another exemplary flexible tube 700 and an array of electrode pairs associated with a plurality of wires disposed within the flexible tube 700. As shown in FIG. 7, flexible tube 700 may comprise an elongated flexible tube 710 that includes a straight portion, instead of a horseshoe-shaped loop portion or a J-shaped loop portion. The straight portion may be located near the distal end of a sheath. In some variations, the elongated flexible tube 710 may comprise a fluid input end 312, a support wire 320, a first wire 340, a first interleaved wire portion 338, a second wire 336, a second interleaved wire portion 334, and a third wire 332. These components are similar to those described above in connection with FIG. 3A and are thus not repeatedly described.

In some variations, the distal end of the elongated flexible tube 710 (e.g., end 714) may be sealed such that the conducive fluid flows in and out through the fluid input end 312. Moreover, a wire associated with the electrode pair closest to the distal end of the tube is configured to extend at least from the sealed distal end of the tube to the open proximal end of the tube. As illustrated in FIG. 7, because the end 714 is sealed, a portion of the third wire 332 may be configured to return to the fluid input end 312 to electrically couple to a negative terminal of a voltage source such as a high voltage pulse generator 102. In some variations, the portion of the third wire 332 that returns to the fluid input end 312 may be configured to be positioned away from the electrode pairs of the interleaved wire portions (e.g., wire portions 334 and 338) such that it does not interfere with the shock wave generated by the electrode pairs. For example, the portion of the third wire 332 that returns to the fluid input end 312 may be configured to be positioned in the opposite side from the side of the arc-generating regions of the interleaved wire portion 338 and 334. In some variations, the elongated flexible tube 710 comprising a straight portion may be configured to be accommodated in a portion of a patient's body that has similar shape (e.g., the patient's knee). Configuring the tube to be similar to the portion of the patient's body to be treated increases the effectiveness of delivering the shock wave and therefore the treatment. In some variations, the elongated flexible tube 710 comprising a straight portion may have a smaller dimension (e.g., length) than the elongated flexible tube 310 comprising a horseshoe-shaped loop portion or the elongated flexible tube 610 comprising a J-shaped curved portion. Smaller dimension may enable the shock wave device to be advanced more easily within the vasculature. In some variations, a single elongated tube (e.g., tube 300, tube 610, tube 710) is carried within the sheath to so that a smaller sheath can be used. It is appreciated that a tube is not limited to the examples described herein and can have any desired shape.

Figure 11A:
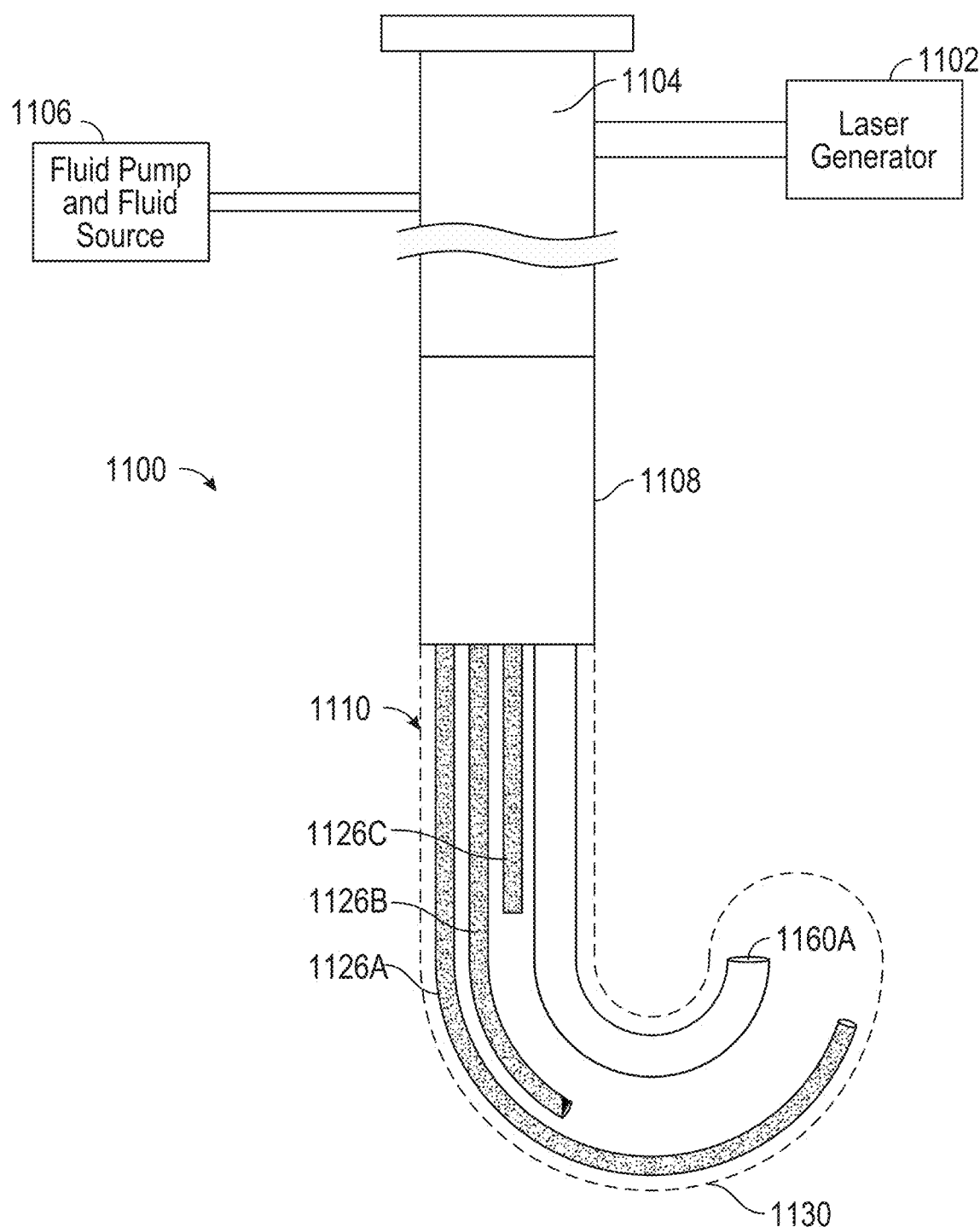
FIG. 11A schematically depicts another exemplary variation of a shock wave device for the treatment of calcified lesions in a heart valve.

FIG. 11A schematically depicts another variation of a shock wave device 1100 for the treatment of calcified lesions in a heart valve. The shock wave device 1100 may comprise an elongated flexible tube 1110. The elongated flexible tube 1110 may be carried by a sheath 1108. At least part of the elongated flexible tubes 1110 may be movably accommodated within the sheath 1108. As illustrated in FIG. 11A, the elongated flexible tube 1110 may be extended beyond the distal end of the sheath 1108 for treating calcified lesions in heart valves. In some variations, the sheath 1108 may be coupled to a proximal handle 1104. The sheath 1108 may be introduced into the vasculature and advanced in a retrograde direction (e.g., via a femoral artery) to a heart valve.

In some variations, the elongated flexible tube 1110 may comprise a fluid input end located near a proximal end of the sheath 1108. A fluid may be introduced via the fluid input end. For example, the fluid may be introduced to the elongated flexible tube 1110 by the fluid pump and fluid source 1106. The fluid pump and fluid source 1106 may fill the elongated flexible tube 1100 with a fluid such as saline or saline/contrast mixture. In some variations, the elongated flexible tube 1110 may have one fluid end, through which the fluid may be introduced to the tube and discharged from the tube.

In some variations, the elongated flexible tube 1100 has a loop portion 1130, which is configured to be at least partially accommodated within a cusp of the heart valve. In the depicted example, the shape of the loop portion may be set by the support wire 1160A and the elongated flexible tube 1110 may be configured to operate in a manner consistent with the method described with reference to FIGS. 9A-E.

One or more shock wave generators are positioned within the loop portion 1130. As depicted in FIG. 11A, the three shock wave generators 1126A-C include three optical fibers of different lengths. Each of the optical fibers is connected to the laser generator 1102. In some examples, each optical fiber is configured to generate shock waves at the distal end of the optical fiber in the fluid in response to laser pulses generated by the laser generator 1102 in a process called thermoelastic expansion. In some examples, an absorber substance is mixed into the fluid (e.g., saline), which is flushed into a part of the vasculature (e.g., artery), so that the laser is absorbed and shock waves are generated at the distal end of the optical fiber. Subsequently, the shock waves propagate from the distal end of the optical fiber through the vessel and to the tissue to be treated. Alternatively, the shock waves are generated at the interface of the target tissue due to pigment absorption. For examples, for excimer lasers, one mechanism for the lasers to act on tissue is via absorption and subsequent microablation. Because this type of lasers do not absorb well in certain fluids (e.g., saline), a part of the vasculature (e.g., artery) is flushed with the fluid (e.g., saline that is not mixed with any absorber substance) to clear out the blood. Subsequently, the laser (in the form of a pulse wave) is propagated through the fluid until the laser encounters pigmented tissue that can absorb energy from the laser. Generally, biological tissue that is calcified or diseased (e.g., vessel endothelium or calcified tissue) can absorb a significant amount of energy at the wavelengths of the lasers. Accordingly, the shock waves are generated at the pigmented tissue rather than at the distal end of the optical fiber, in accordance with some embodiments.

Laser absorption in the fluid leads to a primary pressure wave (shock wave) emitted from the absorption region. After a low fluence threshold, a vapor bubble is also formed. The growth and subsequent collapse of the vapor cavity lead to secondary pressure waves (shock waves). One of ordinary skill in the art would recognize that this process is distinct from the generation of shock waves in FIGS. 1A-C in some aspects. Specifically, the shock wave generation in FIGS. 1A-C is a result of electrohydraulic vapor expansion, which has a different initial process of current discharge and ionization. Nevertheless, in both processes, the shock wave generation ends in a very similar acoustic pressure result and cavitation bubble activity.

Figure 11B:
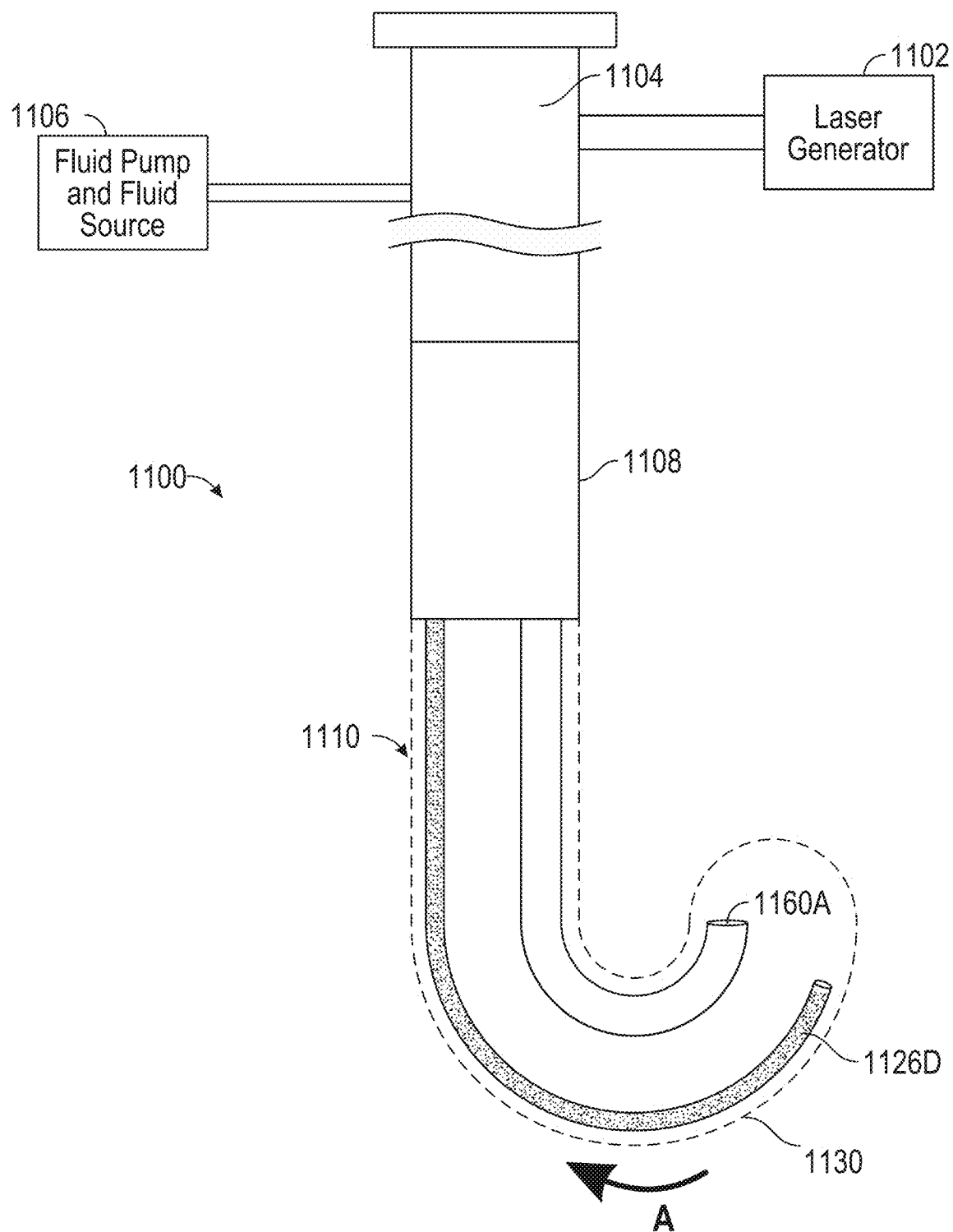
FIG. 11B schematically depicts another exemplary variation of a shock wave device for the treatment of calcified lesions in a heart valve.

In some embodiments, as depicted in FIG. 11B, the elongated flexible tube include an optical fiber 1126D, which is configured to be slidable along the elongated flexible tube. By sliding the optical fiber, the distal end thereof can be positioned at various locations within the tube permitting shock waves to be generated at the desired locations. In one preferred approach, the fiber may be initially positioned so that the distal end of the fiber is close to the distal end of the tube. During the procedure, the fiber can be withdrawn (in the direction of arrow A) allowing shock waves to be generated at increasingly more proximal locations within the tube. This slidable configuration may allow a smaller elongated flexible tube and/or sheath to be used.

While this invention has been particularly shown and described with references to embodiments thereof, it will be understood by those skilled in the art that various changes in form and details may be made therein without departing from the scope of the invention. For all of the embodiments described above, the steps of the methods need not be performed sequentially.

We claim:

1. A device for delivering shock waves to treat calcified lesions in a heart valve, comprising:
    an elongated flexible tube carried by a sheath, the tube having a fluid input end, the fluid input end of the tube being located near a proximal end of the sheath, and wherein the tube includes a loop portion, the loop portion being configured to be at least partially accommodated within a cusp of the heart valve, said tube being fillable with a conductive fluid via the fluid input end of the tube; and
    an array of electrode pairs associated with a plurality of wires positioned within the loop portion, said electrode pairs being electrically connectable to a voltage source and configured to generate shock waves in the conductive fluid in response to voltage pulses.

2. The device of claim 1, wherein the tube is formed from at least one of compliant polymer.

3. The device of claim 1, wherein the electrode pairs are carried by interleaved wire portions electrically coupled in series to convey the voltage pulses.

4. The device of claim 1, wherein the array of electrode pairs are carried by at least two interleaved wire portions coupled in series configured to generate shock waves in response to voltage pulses.

5. The device of claim 1, wherein the electrode pairs comprises a first electrode pair and a second electrode pair,
    wherein the first electrode pair includes a first arc-generating region of a first wire and at least one second arc-generating region of a second wire, a portion of the first wire being interleaved with a first portion of the second wire, the first wire having an electrical potential that is more positive than that of the second wire, and
    wherein the second electrode pair includes a third arc-generating region of the second wire and at least one fourth arc-generating region of a third wire, a second portion of the second wire being interleaved with a first portion of the third wire, the second wire having an electrical potential that is more positive than that of the third wire.

6. The device of claim 5, wherein the first wire is electrically coupled to a positive terminal of the voltage source, and the third wire is electrically coupled to a negative terminal of the voltage source.

7. The device of claim 5, wherein the portion of the first wire interleaves with the first portion of the second wire to form a first coil with a center axis that is common to the portion of the first wire and the first portion of the second wire; and wherein the second portion of the second wire interleaves with the first portion of the third wire to form a second coil with a center axis that is common to the second portion of the second wire and the first portion of the third wire.

8. The device of claim 5, wherein the electrode pairs further comprises a third electrode pair, the third electrode pair including a fifth arc-generating region of the third wire and at least one arc-generating region of a fourth wire, a second portion of the third wire being interleaved with a portion of the fourth wire, the third wire having an electrical potential that is more positive than that of the fourth wire.

9. The device of claim 8, wherein the first wire is electrically coupled to a positive terminal of the voltage source, and the fourth wire is electrically coupled to a negative terminal of the voltage source.

10. The device of claim 9, wherein the second portion of the third wire interleaves with a portion of the fourth wire to form a third coil with a center axis that is common to the second portion of the third wire and the portion of the fourth wire.

11. The device of claim 1, wherein each of the electrode pair comprises one or more arc-generating regions of a first wire portion and one or more arc-generating regions of a second wire portion, the arc-generating regions being devoid of insulation and being configured to generate plasma arcs between two neighboring wire portions to convey the shock waves.

12. The device of claim 11, wherein the first wire portion comprises a smaller number of arc-generating regions than that of the second wire portion, the first wire portion being part of a wire having an electrical potential that is more positive than that of the wire comprising the second wire portion.

13. The device of claim 12, wherein the first wire portion includes one arc-generating region, and the second wire portion includes at least two arc-generating regions, the arc-generating region of the first wire portion being positioned to compensate arc-induced erosion of the insulation of the first wire portion.

14. The device of claim 1, wherein an inner diameter of the tube is in the range of about 0.04 inch to about 0.08 inch.

15. The device claim of 1, further comprising a plurality of spacers configured to space the array of electrode pairs away from the inner wall of the tube.

16. The device of claim 15, the spacers include ring-shaped spacers.

17. The device of claim 1, further comprising an elongated flexible support wire disposed within the tube, wherein the support wire is in contact with the array of electrode pairs to support the electrode pairs.

18. The device of claim 17, wherein the support wire includes an electrical insulator.

19. The device of claim 17, wherein the support wire is formed from polyimide or nitinol.

20. The device of claim 17, further comprising a marker disposed in the loop portion of the tube, the marker being co-axially coupled to the support wire.

21. The device of claim 1, further comprises a fluid source and a fluid pump, the fluid pump being configured to deliver fluid from the fluid source to the fluid input end of the tube.

22. The device of claim 1, further comprising:
    at least one additional elongated flexible tube carried by the sheath; and
    a central anchor extending between and beyond the loop portions of the tubes and configured to pass through the leaflets of the heart valves and into the ventricle to stabilize the position of the sheath.

23. The device of claim 22, wherein the central anchor is a self-expanding anchor.

24. The device of claim 22, wherein the central anchor comprises a shape-memory material.

25. The device of claim 22,
    wherein the central anchor includes a plurality of arms,
    wherein one or more markers in a first configuration are disposed on a first arm of the plurality of arms, and wherein one or more markers in a second configuration are disposed on a second arm of the plurality of arms.

26. The device of claim 25, wherein the first configuration and the second configuration are different in: marker count, marker shape, marker length, marker arrangement on the arm, or a combination thereof.

27. The device of claim 1, wherein the loop portion comprises a horse-shoe shaped loop or a J-shaped loop.

28. A device for delivering shock waves to treat calcified lesions in a heart valve, comprising:
an elongated flexible tube carried by a sheath, the tube having a fluid input end, the fluid input end of the tube being located near a proximal end of the sheath, and wherein the tube includes a loop portion, the loop portion being configured to be at least partially accommodated within a cusp of the heart valve, said tube being fillable with a conductive fluid via the fluid input end of the tube;
an elongated flexible support wire centrally disposed within the tube;
at least two insulated wires supported by the elongated flexible support wire, the at least two insulated wires being coiled around the elongated flexible support wire; and
at least two electrode pairs included in the at least two insulated wires positioned within the loop portion, each of the electrode pairs comprising a plurality of arc-generating regions formed within interleaved portions of two insulated wires of the at least two insulated wires, the arc-generating regions being devoid of insulation, the at least two electrode pairs being electrically connectable to a voltage source and configured to generate shock waves in the conductive fluid in response to voltage pulses.

29. A method for delivering shock waves to treat calcified lesions in a heart valve, comprising:
introducing a shock wave device into a patient's vasculature, the shock wave device comprising an elongated flexible tube carried by a sheath, the tube having a fluid input end, the fluid input end of the tube being located near a proximal end of the sheath, and wherein the tube includes a loop portion, the loop portion being configured to be at least partially accommodated within a cusp of the heart valve, said tube being fillable with a conductive fluid via the fluid input end of the tube; and
an array of electrode pairs associated with a plurality of wires positioned within the loop portion, said electrode pairs being electrically connectable to a voltage source and configured to generate shock waves in the conductive fluid in response to voltage pulses;
advancing the shock wave device within the vasculature such that the loop portion of the tube is at least partially accommodated with a cusp of the heart valve;
providing the tube of the shock wave device with conductive fluid; and
activating the voltage source to apply shock waves to treat the calcified lesions.

30. A device for delivering shock waves to treat calcified lesions in a heart valve, comprising:
an elongated flexible tube carried by a sheath, the tube having a fluid input end, the fluid input end of the tube being located near a proximal end of the sheath, said tube being fillable with a conductive fluid via the fluid input end of the tube; and
an array of electrode pairs associated with a plurality of wires positioned within the tube, said electrode pairs being electrically connectable to a voltage source and configured to generate shock waves in the conductive fluid in response to voltage pulses, wherein the electrode pairs comprises a first electrode pair and a second electrode pair,
wherein the first electrode pair includes a first arc-generating region of a first wire and at least one second arc-generating region of a second wire, a portion of the first wire being interleaved with a first portion of the second wire, the first wire having an electrical potential that is more positive than that of the second wire, and
wherein the second electrode pair includes a third arc-generating region of the second wire and at least one fourth arc-generating region of a third wire, a second portion of the second wire being interleaved with a first portion of the third wire, the second wire having an electrical potential that is more positive than that of the third wire.

31. A device for delivering shock waves to treat calcified lesions in a heart valve comprising:
an elongated flexible tube carried by a sheath,
wherein the tube has an open proximal end and a sealed distal end,
wherein the distal end of the tube is configured to be at least partially accommodated within a cusp of the heart valve, and
wherein the tube is fillable with a pressurized conductive fluid via the open proximal end of the tube; and
an array of electrode pairs associated with a plurality of wires positioned within the tube, said electrode pairs being electrically connectable to a voltage source and configured to generate shock waves in the conductive fluid in response to voltage pulses.

32. The device of claim 31, wherein the tube is J-shaped, wherein the sealed distal end includes a curved portion, and wherein the curved portion is configured to be accommodated within the cusp of the heart valve.

33. The device of claim 31,
wherein each electrode pair of the array is associated with a first wire and a second wire interleaved in a coiled configuration, the first wire having an electrical potential that is more positive than that of the second wire,
wherein the second wire associated with the electrode pair closest to the distal end of the tube is configured to extend at least from the sealed distal end of the tube to the open proximal end of the tube.

34. The device of claim 31, further comprising:
a central anchor extending beyond the sealed distal end of the tube and configured to pass through the leaflets of the heart valves and into the ventricle to stabilize the position of the sheath.

35. The device of claim 34,
wherein the central anchor includes a plurality of arms,
wherein one or more markers in a first configuration are disposed on a first arm of the plurality of arms, and
wherein one or more markers in a second configuration are disposed on a second arm of the plurality of arms.

36. The device of claim 35, wherein the first configuration and the second configuration are different in: marker count, marker shape, marker length, marker arrangement on the arm, or a combination thereof.

37. A method for delivering shock waves to treat calcified lesions in a heart valve, comprising:
introducing a shock wave device into a patient's vasculature, wherein the shock wave device comprises:
an elongated flexible tube carried by a sheath, wherein the tube includes an open proximal end and a sealed distal end, wherein the distal end of the tube is configured to curl into a loop portion when extended out of the sheath, wherein the loop portion is configured to partially unfold when said tube is filled with a pressurized conductive fluid via the open proximal end of the tube; and an array of electrode pairs associated with a plurality of wires positioned within the loop portion, said electrode pairs being electrically connectable to a voltage source and configured to generate shock waves in the conductive fluid in response to voltage pulses;

positioning the distal end of the sheath close to but spaced from a cusp of the heart valve;

extending a portion of the tube out of the sheath such that the distal end of the tube curls into a loop portion and such that the loop portion of the tube is at least partially accommodated within the cusp of the heart valve;

pressurizing the tube with a pressurized conductive fluid via the open proximal end to partially unfold the loop portion of the tube into a curved portion; and activating the voltage source to apply shock waves to treat the calcified lesions.

38. A method for delivering shock waves to treat calcified lesions in a heart valve, comprising:
introducing a shock wave device into a patient's vasculature, the shock wave device comprising:
an elongated flexible tube carried by a sheath, the tube having a proximal end and a distal end, wherein the distal end of the tube is configured to be at least partially accommodated within a cusp of the heart valve, and wherein the tube is fillable with a conductive fluid,
an array of electrode pairs associated with a plurality of wires positioned within the tube, said electrode pairs being electrically connectable to a voltage source and configured to generate shock waves in the conductive fluid in response to voltage pulses, and
a central anchor extending beyond the distal end of the tube and configured to pass through the leaflets of the heart valves and into the ventricle to stabilize the position of the sheath, wherein the anchor includes a first arm and a second arm, wherein one or more markers are disposed on the first arm in a first configuration and one or more markers are disposed on the second arm in a second configuration;
advancing the shock wave device within the vasculature such that the central anchor is placed into the ventricle;
expanding the central anchor;
based on the marker configurations, determining the locations of the arms;
based on the determined locations of the arms, positioning the tube such that the distal end of the tube is at least partially accommodated with a first cusp of the heart valve;
activating the voltage source to apply shock waves to treat the calcified lesions.

39. The method of claim 38, further comprising:
repositioning the tube based on the determined locations such that the distal end of the tube is at least partially accommodated with a second cusp of the heart valve;
activating the voltage source to apply shock waves to treat the calcified lesions.

40. The device of claim 38, wherein the first configuration and the second configuration are different in: marker count, marker shape, marker length, marker arrangement on the arm, or a combination thereof.

41. A device for delivering shock waves to treat calcified lesions in a heart valve, comprising:
an elongated flexible tube carried by a sheath, the tube having a fluid input end, the fluid input end of the tube being located near a proximal end of the sheath, and wherein the tube includes a loop portion, the loop portion being configured to be at least partially accommodated within a cusp of the heart valve, said tube being fillable with a conductive fluid via the fluid input end of the tube; and
one or more shock wave generators positioned within the loop portion, said one or more shock wave generators being connectable to a power source and configured to generate shock waves in the conductive fluid in response to pulse energy.

42. The device of claim 41,
wherein the one or more shock wave generators include an array of electrode pairs associated with a plurality of wires positioned within the loop portion, and
wherein the power source includes a voltage source and wherein the pulse energy includes voltage pulses.

43. The device of claim 41, wherein the one or more shock wave generators include a first optical fiber having a first length and a second optical fiber having a second length different from the first length.

44. The device of claim 41, wherein the power source includes a laser generator and wherein the pulse energy includes shock waves and pressure pulses generated by laser pulses.

45. The device of claim 41, wherein the one or more shock wave generators include an optical fiber, wherein the optical fiber is configured to be slidable along the elongated flexible tube to generate shock waves at different locations.

* * * * *